(12) United States Patent
Chao Lee

(10) Patent No.: US 11,458,181 B2
(45) Date of Patent: Oct. 4, 2022

(54) HERBAL FORMULA USED FOR PREPARING PHARMACEUTICAL COMPOSITION FOR PREVENTING AND TREATING METABOLIC SYNDROME

(71) Applicant: Ying-Jih Chao Lee, Taipei (TW)

(72) Inventor: Ying-Jih Chao Lee, Taipei (TW)

( * ) Notice: Subject to any disclaimer, the term of this patent is extended or adjusted under 35 U.S.C. 154(b) by 327 days.

(21) Appl. No.: 16/881,006

(22) Filed: May 22, 2020

(65) Prior Publication Data
US 2020/0368305 A1    Nov. 26, 2020

(30) Foreign Application Priority Data

May 22, 2019 (TW) .................................. 108117608
Sep. 25, 2019 (TW) .................................. 108134506

(51) Int. Cl.

| | | |
|---|---|---|
| *A61K 36/64* | (2006.01) | |
| *A61K 36/40* | (2006.01) | |
| *A61K 36/8945* | (2006.01) | |
| *A61K 36/884* | (2006.01) | |
| *A61P 3/06* | (2006.01) | |
| *A61K 36/076* | (2006.01) | |
| *A61K 36/714* | (2006.01) | |
| *A61K 36/54* | (2006.01) | |
| *A61K 36/65* | (2006.01) | |

(52) U.S. Cl.
CPC ............ *A61K 36/64* (2013.01); *A61K 36/076* (2013.01); *A61K 36/40* (2013.01); *A61K 36/54* (2013.01); *A61K 36/65* (2013.01); *A61K 36/714* (2013.01); *A61K 36/884* (2013.01); *A61K 36/8945* (2013.01); *A61P 3/06* (2018.01)

(58) Field of Classification Search
CPC ......... A61P 3/06; A61K 36/076; A61K 36/40; A61K 36/54; A61K 36/65; A61K 36/714; A61K 36/884; A61K 36/8945
See application file for complete search history.

(56) References Cited

FOREIGN PATENT DOCUMENTS

JP     2020189838 A  * 11/2020 ........... A61K 36/076

* cited by examiner

*Primary Examiner* — Aaron J Kosar
(74) *Attorney, Agent, or Firm* — Li & Cai Intellectual Property Office

(57) ABSTRACT

An herbal formula used for preparing a pharmaceutical composition for preventing and treating metabolic syndrome is provided. The herbal formula includes *Rehmanniae radix preparata, Cornus officinalis, Dioscorea polystachya, Alisma plantago-aquatica, Paeonia suffruticosa, Poria cocos, Aconitum carmichaeli,* and *Cinnamomum cassia.*

8 Claims, 36 Drawing Sheets

HERBAL FORMULA USED FOR PREPARING PHARMACEUTICAL COMPOSITION FOR PREVENTING AND TREATING METABOLIC SYNDROME

CROSS-REFERENCE TO RELATED PATENT APPLICATION

This application claims the benefit of priority to Taiwan Patent Application Nos. 108117608 and 108134506, filed on May 22, 2019 and Sep. 25, 2019, respectively. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to an herbal formula, and more particularly to an herbal formula used for preparing a pharmaceutical composition for preventing and treating metabolic syndrome.

BACKGROUND OF THE DISCLOSURE

Statins, cholesterol synthesis inhibitors, are the cholesterol-lowering drugs of choice. Statin can effectively reduce cholesterol and low-density lipoprotein cholesterol (LDL-C) to achieve reduction in the incidence of coronary heart disease and the mortality of stroke patients. Although statins can reduce cholesterol in the blood, it cannot effectively reduce triglycerides in the blood, and may cause other side effects. In addition, according to research, statins may increase the risk of patients getting diabetes, that is, statins may interfere with blood sugar balance.

In conventional techniques, statin is often used in combination with fibric acid derivatives (fibrates) to treat hyperlipidemia. Fibric acid derivatives mainly regulate the metabolism of cytochrome P450 (CYP) in the liver by activating peroxisome proliferator-activated receptor alpha (PPAR-α) and PPAR-β, thereby reducing triglycerides and increasing high-density lipoprotein cholesterol (HDL-C). However, fibric acid derivatives cannot reduce cholesterol in the blood.

According to research, both statin and fibric acid derivatives have side effects that may cause rhabdomyolysis, and patients with liver and kidney dysfunction are not suitable candidates for the combination therapy of statin and fibric acid derivatives. In addition, generally speaking, compared with traditional Chinese medicine, although the therapeutic effect of western medicine is more significant, numerous side effects may also easily occur therefrom. Therefore, the effective usage of natural (or herbal) medicine has become one of the more important issues to be solved in this field.

SUMMARY OF THE DISCLOSURE

In response to the above-referenced technical inadequacies, the present disclosure provides an herbal formula used for preparing a pharmaceutical composition for preventing and treating metabolic syndrome.

In one aspect, the present disclosure provides an herbal formula used for preparing a pharmaceutical composition for preventing and treating metabolic syndrome. The herbal formula includes *Rehmanniae radix preparata, Cornus officinalis, Dioscorea polystachya, Alisma plantago-aquatica, Paeonia suffruticosa, Poria cocos, Aconitum carmichaeli,* and *Cinnamomum cassia.*

In certain embodiments, the herbal formula is composed of the following components: 25-35 wt % of *Rehmanniae radix preparata,* 12-18 wt % of *Cornus officinalis,* 12-18 wt % of *Dioscorea polystachya,* 7-13 wt % of *Alisma plantago-aquatica,* 7-13 wt % of *Paeonia suffruticosa,* 7-13 wt % of *Poria cocos,* 2-6 wt % of *Aconitum carmichaeli,* and 2-6 wt % of *Cinnamomum cassia.*

In certain embodiments, the herbal formula is composed of the following components: 29.6 wt % of *Rehmanniae radix preparata,* 14.8 wt % of *Cornus officinalis,* 14.8 wt % of *Dioscorea polystachya,* 11.1 wt % of *Alisma plantago-aquatica,* 11.1 wt % of *Paeonia suffruticosa,* 11.1 wt % of *Poria cocos,* 3.7 wt % of *Aconitum carmichaeli,* and 3.7 wt % of *Cinnamomum cassia.*

In certain embodiments, the prevention and treatment of metabolic syndrome refers to therapeutic effects that are capable of improving conditions of overweight, hyperglycemia, fatty liver, dyslipidemia, hypercholesterolemia, or hypertriglyceridemia.

In certain embodiments, the prevention and treatment of metabolic syndrome is achieved by the simultaneous inhibition of 3-hydroxy-3-methylglutaryl coenzyme A reductase and cholesteryl ester transfer protein by the herbal formula.

In certain embodiments, the pharmaceutical composition is administered orally to a recipient at 10-40 g per day.

In certain embodiments, the dosage form of the pharmaceutical composition is powder, water extract solution, suspension, emulsion, syrup, pill, tablet, hydrogel, or capsule.

In certain embodiments, the pharmaceutical composition further includes a pharmaceutically acceptable adjuvant.

Therefore, the herbal formula used for preparing the pharmaceutical composition for preventing and treating metabolic syndrome of the present disclosure can improve conditions of overweight, hyperglycemia, fatty liver, dyslipidemia, hypercholesterolemia, or hypertriglyceridemia.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
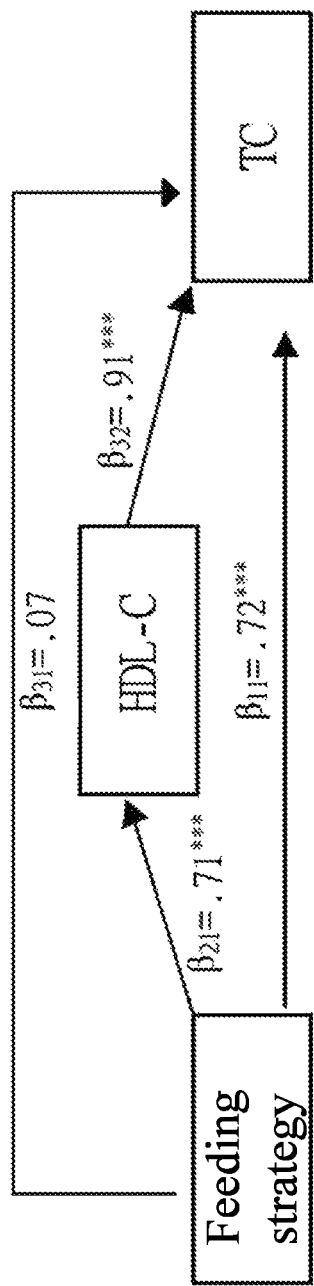
FIGS. 1 to 8 are diagrams of multiple regression mediation of the herbal formula of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

A first embodiment of the present disclosure provides an herbal formula. The herbal formula includes *Rehmanniae radix preparata*, *Cornus officinalis*, *Dioscorea polystachya*, *Alisma plantago-aquatica*, *Paeonia suffruticosa*, *Poria cocos*, *Aconitum carmichaeli*, and *Cinnamomum cassia*.

Further, the herbal formula is at least composed of the following components: 25-35 wt % of *Rehmanniae radix preparata*, 12-18 wt % of *Cornus officinalis*, 12-18 wt % of *Dioscorea polystachya*, 7-13 wt % of *Alisma plantago-aquatica*, 7-13 wt % of *Paeonia suffruticosa*, 7-13 wt % of *Poria cocos*, 2-6 wt % of *Aconitum carmichaeli*, and 2-6 wt % of *Cinnamomum cassia*. Preferably, the herbal formula is composed of the following components: 29.6 wt % of *Rehmanniae radix preparata*, 14.8 wt % of *Cornus officinalis*, 14.8 wt % of *Dioscorea polystachya*, 11.1 wt % of *Alisma plantago-aquatica*, 11.1 wt % of *Paeonia suffruticosa*, 11.1 wt % of *Poria cocos*, 3.7 wt % of *Aconitum carmichaeli*, and 3.7 wt % of *Cinnamomum cassia*.

The formula ratio of the herbal formula in grams is as shown in Table 1.

TABLE 1

The formula ratio of the herbal formula in grams. (Unit: g)

| Herbal formula | Dose range | High dose | Low dose |
|---|---|---|---|
| total weight | 30 | 27 | 13.5 |
| Rehmanniae radix preparata | 7.5-10.5 | 8 | 4 |
| Cornus officinalis | 3.6-5.4 | 4 | 2 |
| Dioscorea polystachya | 3.6-5.4 | 4 | 2 |
| Alisma plantago-aquatica | 2.1-3.9 | 3 | 1.5 |
| Paeonia suffruticosa | 2.1-3.9 | 3 | 1.5 |
| Poria cocos | 2.1-3.9 | 3 | 1.5 |
| Aconitum carmichaeli | 0.6-1.8 | 1 | 0.5 |
| Cinnamomum cassia | 0.6-1.8 | 1 | 0.5 |

Taking the total weight of the herbal formula as 30 g for instance, it can include the following components: 7.5-10.5 g of *Rehmanniae radix preparata*, 3.6-5.4 g of *Cornus officinalis*, 3.6-5.4 g of *Dioscorea polystachya*, 2.1-3.9 g of *Alisma plantago-aquatica*, 2.1-3.9 g of *Paeonia suffruticosa*, 2.1-3.9 g of *Poria cocos*, 0.6-1.8 g of *Aconitum carmichaeli*, and 0.6-1.8 g of *Cinnamomum cassia*.

In this embodiment, the herbal formula with a total weight of 27 g was used as the high-dose group (H), which includes the following components: 8 g of *Rehmanniae radix preparata*, 4 g of *Cornus officinalis*, 4 g of *Dioscorea polystachya*, 3 g of *Alisma plantago-aquatica*, 3 g of *Paeonia suffruticosa*, 3 g of *Poria cocos*, 1 g of *Aconitum carmichaeli*, and 1 g of *Cinnamomum cassia*. The method of administration to adults (body weight 60 kg) is 27 g orally per day. Using the Meeh-Rubner formula for conversion, rats are given 2 g/kg orally per day.

In this embodiment, the herbal formula with a total weight of 13.5 g was used as the low-dose group (L), which includes the following components: 4 g of *Rehmanniae radix preparata*, 2 g of *Cornus officinalis*, 2 g of *Dioscorea polystachya*, 1.5 g of *Alisma plantago-aquatica*, 1.5 g of *Paeonia suffruticosa*, 1.5 g of *Poria cocos*, 0.5 g of *Aconitum carmichaeli*, and 0.5 g of *Cinnamomum cassia*. The method of administration to adults (body weight 60 kg) is 13.5 g orally per day. Using the Meeh-Rubner formula for conversion, rats are given 1 g/kg orally per day.

Specifically speaking, the herbal formula can be used to prepare a pharmaceutical composition for preventing and treating metabolic syndrome. The pharmaceutical composition can include the herbal formula and a pharmaceutically acceptable adjuvant. As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

For instance, the material of the pharmaceutically acceptable adjuvant can include sugars (lactose, glucose, and sucrose), starches (corn starch and potato starch), cellulose and its derivatives (sodium carboxymethyl cellulose, ethyl cellulose and cellulose acetate), gelatin, talc, excipients (cocoa butter, suppository wax), oils (peanut oil, cottonseed oil, safflower oil, sesame oil, olive oil, corn oil, soybean oil), glycols (propylene glycol), polyols (glycerin, sorbitol, mannitol, polyethylene glycol), esters, buffers, and so on, but is not limited thereto.

For instance, the dosage form of the pharmaceutical composition can be powder, water extract solution, suspension, emulsion, syrup, pill, tablet, hydrogel, or capsule, but is not limited thereto.

Furthermore, the method of administering the pharmaceutical composition to an adult (weight 60 kg) may be 10-40 g orally per day, preferably 12-30 g.

Second Embodiment

In this embodiment, the feeding strategies is divided into four groups, which respectively are a basic group (B), a control group (C), a low-dose group (L), and a high-dose group (H), and the expected index content ratio of these groups is 1.0:4.0:3.0:2.0. Therefore, 29 Sprague-Dawley (SD) rats (5 weeks old, body weight 100-125 g, male) are randomly divided into 2 groups, of which 8 are the basic group (B) and the other 21 are the high-fructose feeding group (HF). The basic group (B) feeding strategy is common commercial feed (Purina® 5001 rodent chow diet), and the feeding strategy of the high fructose feeding group (HF) is a common commercial feed supplemented with 60% fructose so as to induce metabolic syndrome in rats.

Specifically speaking, the feeding strategy of the basic group (B) is to feed with common commercial feed (Purina® 5001 rodent chow diet) and ultrapure water for 4 consecutive weeks. After 4 weeks, continue to feed with normal commercial feed and ultrapure water feeding for 10 weeks.

In addition, the high fructose feeding group (HF) is randomly divided into the control group (C), the low-dose group (L), and the high-dose group (H).

In the control group (C), 7 rats are firstly fed with common commercial feed supplemented with 60% fructose and ultrapure water for 4 consecutive weeks, so as to induce metabolic syndrome. After that, the control group (C) is fed with normal commercial feed supplemented with 60% fructose and ultrapure water feeding for 10 consecutive weeks.

In the low-dose group (L), 7 rats are firstly fed with common commercial feed supplemented with 60% fructose and ultrapure water for 4 consecutive weeks, so as to induce metabolic syndrome. After that, the low-dose group (L) is fed with normal commercial feed supplemented with 60% fructose, 1 g/kg of the low dose of the herbal formula in the first embodiment, and ultrapure water feeding for 10 consecutive weeks.

In the high-dose group (H), 7 rats are firstly fed with common commercial feed supplemented with 60% fructose and ultrapure water for 4 consecutive weeks, so as to induce metabolic syndrome. After that, the high-dose group (H) is fed with normal commercial feed supplemented with 60% fructose, 2 g/kg of the high dose of the herbal formula in the first embodiment, and ultrapure water feeding for 10 consecutive weeks.

After the feeding strategies are completed, rats are sacrificed and are collected and relevant results analyzed. Relevant data results include tissue organ weight and ratio, biochemical index content and triglyceride and cholesterol content in liver.

Specifically speaking, the tissue organ weight and ratio includes body weight, liver weight, ratio of liver weight per 100 g of body weight, abdominal fat weight, and ratio of abdominal fat weight per 100 g of body weight. Biochemical index content includes glucose level, insulin level, homeostatic model assessment for insulin resistance (HOMA-IR), triglyceride in plasma (TG/plasma), cholesterol in plasma (TC/plasma), high-density lipoprotein cholesterol (HDL-C), and low-density lipoprotein cholesterol (LDL-C). In addition, triglyceride and cholesterol content in liver include triglyceride in Liver [TG in Liver, TG(Liver)], Total TG in Liver [Total TG(Liver)], cholesterol in liver [TC in Liver, TC(Liver)], and [Total TC in Liver, Total TC(Liver)].

However, the aforementioned description for the composite nanometer material structure 2 of the first embodiment is merely an example and is not meant to limit the scope of the present disclosure.

Experimental Results

Table 2 is a corrected descriptive statistical table of the above relevant data results. In Table 2, the group ratio is used for descriptive statistical analysis. The group ratio includes equal ratio (also called expected organ weight ratio) and arithmetical ratio (also called expected index content ratio). Compared with the basic group (B), the control group (C), the low-dose group (L) and the high-dose group (H), the expected organ weight group ratio is 1:1:1:1, in which there is no significant difference between the groups of ideal expected equivalent variance mapping functions, and the expected index content ratio is 1:4:2:3, in which there is a significant difference between the groups of ideal expected hierarchical variance mapping functions. The feeding strategy is mapped into a function mapping relationship, and each expected hierarchical variance is expected to have a significant difference, which means that the expected index content ratio reaches the expected hierarchical variance mapping function.

As shown in Table 2, the ratio of body weight of the basic group (B), the control group (C), the low-dose group (L) and the high-dose group (H) is approximately equal to 1.0:1.0:1.0:0.5.

TABLE 2

Corrected descriptive statistical table of the relevant data results.

| Items (unit) | (B) | (C) | (L) | (H) | (B) | (C) | (L) | (H) |
|---|---|---|---|---|---|---|---|---|
| | Expected organ weight ratio: | | | | 1 | 1 | 1 | 1 |
| Body weight (g) | 508.1 | 513.8 | 510.6 | 461.2 | 1.0 | 1.0 | 1.0 | 0.5 |
| Liver weight (g) | 13.0 | 13.1 | 12.6 | 11.6 | 1.0 | 1.0 | 0.9 | 0.6 |
| Ratio of liver weight per 100 g of body weight (%) | 2.6 | 2.5 | 2.5 | 2.5 | 1.0 | 0.9 | 0.9 | 0.9 |
| Abdominal fat weight (g) | 24.0 | 33.8 | 27.4 | 20.6 | 1.0 | 4.0 | 2.0 | −0.1 |

TABLE 2-continued

Corrected descriptive statistical table of the relevant data results.

| | | | | | | | | |
|---|---|---|---|---|---|---|---|---|
| Ratio of abdominal fat weight per 100 g of body weight (%) | 4.7 | 6.5 | 5.3 | 4.4 | 1.0 | 4.0 | 2.0 | 0.5 |

| | Expected index content ratio: | | | | 1 | 4 | 3 | 2 |
|---|---|---|---|---|---|---|---|---|
| Glucose level (mg/dl) | 103.5 | 109.4 | 102.3 | 103.4 | 1.0 | 4.0 | 0.4 | 1.0 |
| Insulin level (ng/dl) | 0.38 | 1.00 | 0.46 | 0.51 | 1.0 | 4.0 | 1.4 | 1.6 |
| HOMA-IR | 2.3 | 6.5 | 2.7 | 3.2 | 1.0 | 4.0 | 1.3 | 1.6 |
| TG/plasma (mg/dl) | 73.1 | 150.7 | 98.1 | 95.2 | 1.0 | 4.0 | 2.0 | 1.9 |
| TC/plasma (mg/dl) | 63.9 | 113.0 | 87.1 | 79.5 | 1.0 | 4.0 | 2.4 | 2.0 |
| HDL-C (mg/dL) | 44.5 | 75.7 | 61.8 | 56.75 | 1.0 | 4.0 | 2.7 | 2.2 |
| LDL-C (mg/dL) | 11.7 | 20.5 | 15.8 | 9.43 | 1.0 | 4.0 | 2.4 | 0.2 |
| HDL-C/TC | 0.71 | 0.67 | 0.71 | 0.72 | 1.0 | 0.9 | 1.0 | 1.0 |
| LDL-C/TC | 0.18 | 0.18 | 0.18 | 0.12 | 1.0 | 1.0 | 1.0 | −2.0 |
| HDL-C/TG | 0.61 | 0.50 | 0.63 | 0.60 | 1.0 | 0.0 | 1.0 | 1.0 |
| TG(Liver) (mg/dL) | 16.7 | 25.4 | 22.7 | 17.5 | 1.0 | 4.0 | 3.1 | 1.3 |
| Total TG(Liver) (mg/dL) | 219.0 | 335.1 | 238.5 | 204.2 | 1.0 | 4.0 | 1.6 | 0.8 |
| TC(Liver) (mg/dL) | 8.7 | 9.1 | 8.9 | 8.2 | 1.0 | 4.0 | 2.9 | −1.7 |
| Total TC(Liver) (mg/dL) | 112.2 | 118.4 | 118.6 | 94.7 | 1.0 | 4.0 | 4.0 | −2.6 |

Table 3 is the independent sample t-test table of the relevant data results. In Table 3, "*" represents a significant difference from the basic group (B), "#" represents a significant difference from the control group (C), and "§" represents a significant difference from the low-dose group (L). If there is none of the above symbols (blank), it means that there is no significant difference between the groups.

TABLE 3

Independent sample t-test table of the relevant data results.

| Items (unit) | Basic group (B) | Control group (C) | Low-dose group (L) | High-dose group (H) |
|---|---|---|---|---|
| Body weight (g) | 508.1 ± 48.7 | 513.8 ± 39.2 | 510.6 ± 25.1 | 461.2 ± 32.8*#§ |
| Liver weight (g) | 13.0 ± 1.6 | 13.1 ± 1.5 | 12.6 ± 0.8 | 11.6 ± 1.1 |
| Ratio of liver weight per 100 g of body weight (%) | 2.6 ± 0.2 | 2.5 ± 0.2 | 2.5 ± 0.1 | 2.5 ± 0.2 |
| Abdominal fat weight (g) | 24.0 ± 5.5 | 33.8 ± 8.6* | 27.4 ± 8.9 | 20.6 ± 7.1# |
| Ratio of abdominal fat weight per 100 g of body weight (%) | 4.7 ± 1.0 | 6.5 ± 1.2* | 5.3 ± 1.6 | 4.4 ± 1.4# |
| Glucose level (mg/dl) | 103.5 ± 7.8 | 109.4 ± 13.2 | 102.3 ± 8.4 | 103.4 ± 6.2 |
| Insulin level (ng/dl) | 0.38 ± 0.21 | 1.00 ± 0.32* | 0.46 ± 0.23# | 0.51 ± 0.26# |
| HOMA-IR | 2.3 ± 1.3 | 6.5 ± 2.7* | 2.7 ± 1.2# | 3.2 ± 1.6# |
| TG/plasma (mg/dl) | 73.1 ± 14.7 | 150.7 ± 33.6* | 98.1 ± 31.3# | 95.2 ± 25.7# |
| TC/plasma (mg/dl) | 63.9 ± 11.1 | 113.0 ± 20.4* | 87.1 ± 15.5*# | 79.5 ± 23.9# |
| HDL-C (mg/dL) | 44.5 ± 4.9 | 75.7 ± 14.9* | 61.8 ± 11.1* | 56.8 ± 14.8*# |
| LDL-C (mg/dL) | 11.7 ± 6.7 | 20.5 ± 5.5* | 15.8 ± 6.7 | 9.4 ± 3.8#§ |
| TG (Liver) (mg/dL) | 16.7 ± 3.4 | 25.4 ± 9.0* | 22.7 ± 11.0 | 17.5 ± 4.6 |
| Total TG (Liver) (mg/dL) | 219.0 ± 58.4 | 335.1 ± 122.4* | 238.5 ± 72.2 | 204.2 ± 66.7# |
| TC (Liver) (mg/dL) | 8.7 ± 1.5 | 9.1 ± 1.0 | 8.9 ± 1.6 | 8.2 ± 0.9 |
| Total TC (Liver) (mg/dL) | 112.2 ± 16.9 | 118.4 ± 14.9 | 118.6 ± 29.7 | 94.7 ± 13.3*# |

As shown in Table 3, in the item of the body weight, the control group (C) is blank, the low-dose group (L) is blank, and the high-dose group (H) is marked * #§; that is, compared with other groups, the high-dose group (H) has significantly lost body weight. Therefore, the high-dose of the herbal formula has a body weight-loss effect.

As shown in Table 2, the ratio of blood glucose level in the basic group (B), control group (C), the low-dose group (L), and the high-dose group (H) is approximately equal to 1.0:4.0:0.4:1.0, the ratio of insulin level is approximately equal to 1.0:4.0:1.4:1.6, and the ratio of HOMA-IR is approximately equal to 1.0:4.0:1.3:1.6. As shown in Table 3, in the items of insulin level and HOMA-IR, the low-dose group (L) and the high-dose group (H) both are marked as #; that is, compared with the control group (C), the low-dose Group (L) and high-dose group (H) significantly reduced insulin secretion. Therefore, the low-dose and high-dose of the herbal formulas have the effect of preventing and treating diabetes.

As shown in Table 3, in the item of the triglyceride in plasma, the low-dose group (L) and the high-dose group (H) are marked as #. In the item of the cholesterol in plasma, the low-dose group (L) is marked as * # and the high-dose group (H) is marked as #. In the item of the total triglyceride in liver, the high-dose group (H) is marked as #. In the item of the item of total cholesterol in liver, the high-dose group (H) is marked as * #. These results indicate that the low-dose and high-dose of the herbal formulas have the effect of preventing and treating fatty liver, and the effect of the high-dose of the herbal formula is more significant.

As shown in Table 3, in the independent sample t test, the relevant data results of the high-dose group (H) which has a significant difference compared to the control group (C) (marked as #) includes the abdominal fat weight, the ratio of abdominal fat weight per 100 g of body weight, the insulin level, the HOMA-IR, the triglyceride in plasma, the cholesterol in plasma, HDL-C, LDL-C, the total TG in the liver, and the total TC in the liver. The relevant data results of the low-dose group (L) which has a significant difference compared to the control group (C) (marked as #) includes the insulin level, the HOMA-IR, the triglyceride in plasma, and the cholesterol in plasma. It is worth mentioning that, in Table 3, although there is no statistically significant difference, compared with the control group (C), the abdominal fat weight, abdominal fat weight ratio, LDL-C, and total TG in the liver of the low-dose group (L) still decreased. These results indicate that the low-dose and high-dose of the herbal formulas have an effect of improving the metabolic syndrome, and the effect of the high-dose of the herbal formula is more significant.

Further, the pharmaceutical composition prepared by the herbal formula of the present disclosure establishes a simultaneous relationship between lipoprotein and lipid metabolism.

When performing the multiple regression mediation, the path coefficients are used as the explanatory power, and the feeding strategy is a function of the equivalent variation and hierarchical variance of the mapping relationship. Simple regression analysis can be used to explain the variance of the mediators and dependent variables in the measurement of the coefficient of determination can be explained by the variation of the independent variable feeding strategy, and the feeding strategy has a significant mapping relationship between the mediator and the dependent variable.

The analysis is based on either the carrier corresponding to the cargo or the carrier not corresponding to the cargo. The relationship of simultaneous group individual factor in the form of carrier or cargo corresponds to whether another simultaneous group individual factor in the form of cargo or carrier has not established a mediation pathway, the purpose being that the cargo does not have a carrier coupling relationship through the carrier. The relationship of simultaneous group individual factor in the form of carrier or cargo corresponds to whether another simultaneous group individual factor in the form of cargo or carrier has established a partial mediating pathway, the purpose being that the cargo partially has a carrier coupling relationship through the carrier, the cargo forms a carrier coupling relationship partially through the carrier, or the cargo leaves the carrier coupling relationship partially through the carrier. The relationship of simultaneous group individual factor in the form of carrier or cargo corresponds to whether another simultaneous group individual factor in the form of cargo or carrier has established a complete mediating pathway, the purpose being that the cargo completely has a carrier coupling relationship through the carrier, the cargo form a carrier coupling relationship completely through the carrier, or the cargo leaves the carrier coupling relationship completely through the carrier.

Referring to FIG. 1 to FIG. 8, diagrams of the multiple regression mediation are performed by the feeding strategies established the complex relationship between lipoprotein and lipid metabolism, referred to as regression mediation. Using exploratory simultaneous group mediation node rules and simultaneous groups for multiple regression mediation verifications, the results are as follows.

Referring to FIG. 1, HDL has a complete mediation effect on the effect of feeding strategies on TC.

Figure 2:
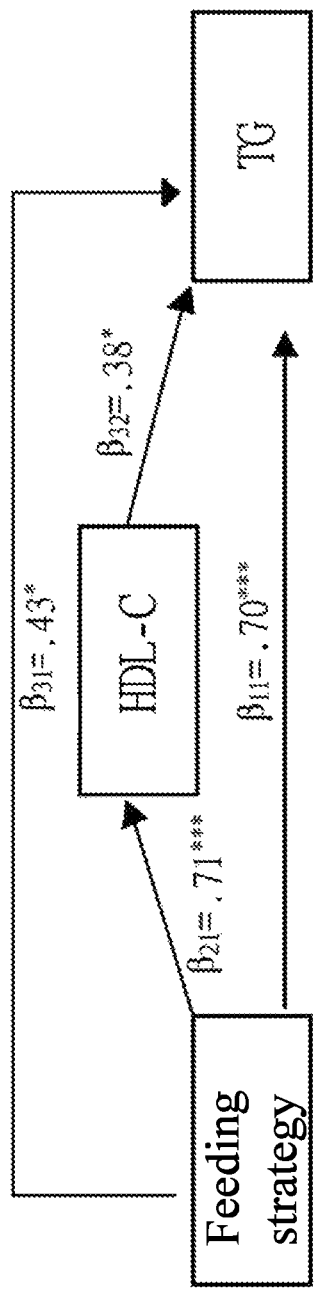

Referring to FIG. 2, HDL has a partial mediation effect on the effect of feeding strategies on TG.

Figure 3:
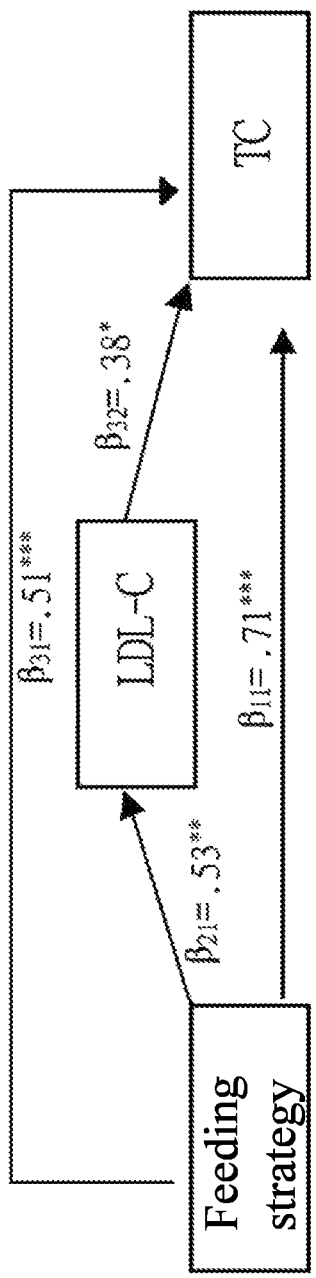

Referring to FIG. 3, LDL has a partial mediation effect on the effect of feeding strategies on TC.

Figure 4:
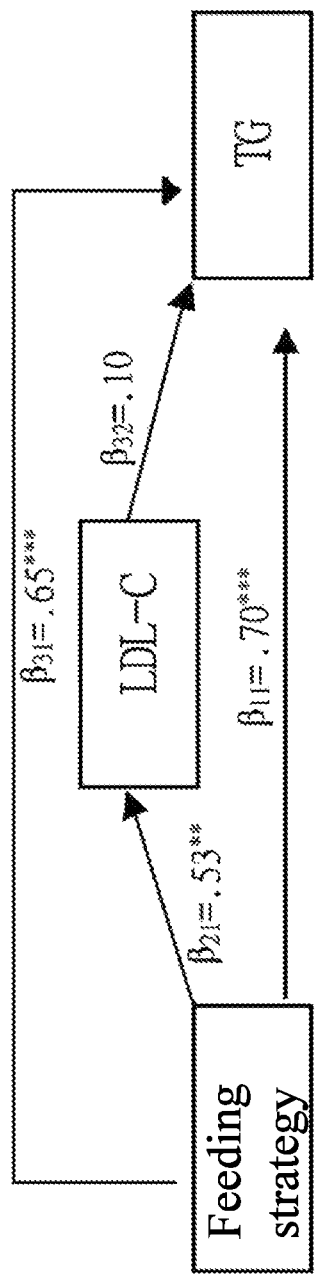

Referring to FIG. 4, LDL has no mediation effect on the effect of feeding strategies on TG.

Figure 5:
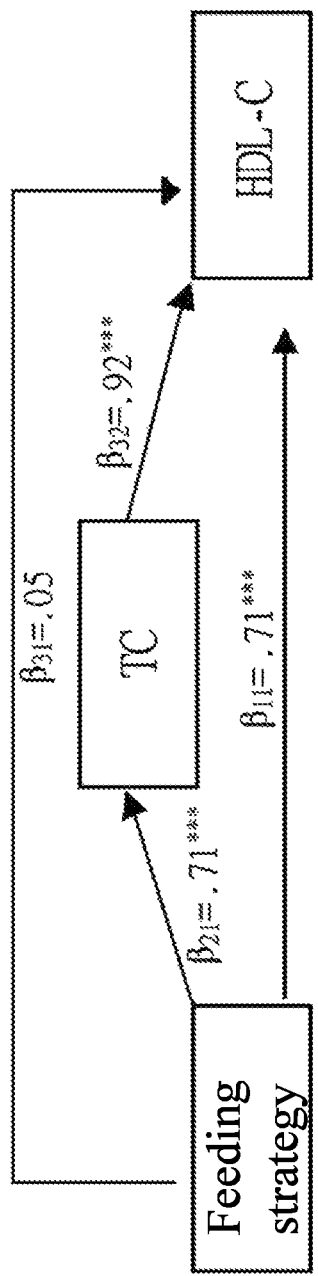

Referring to FIG. 5, TC has a complete mediation effect on the effect of feeding strategies on HDL.

Figure 6:
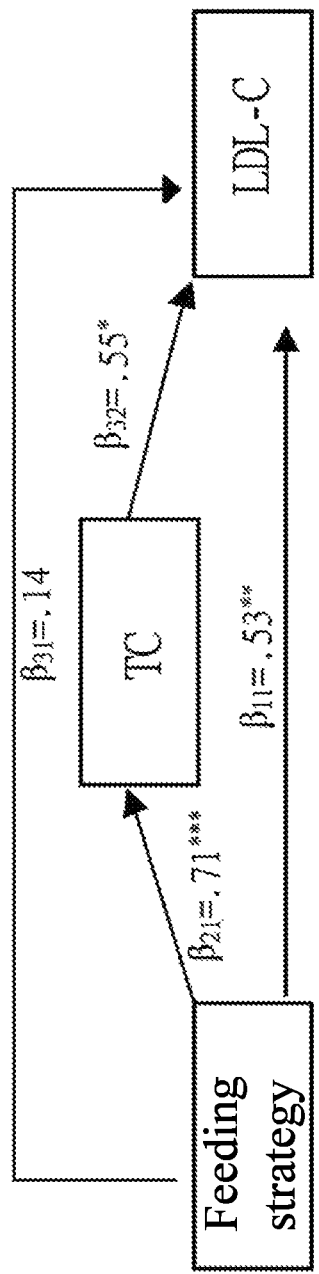

Referring to FIG. 6, TC has a complete mediation effect on the effect of feeding strategies on LDL.

Figure 7:
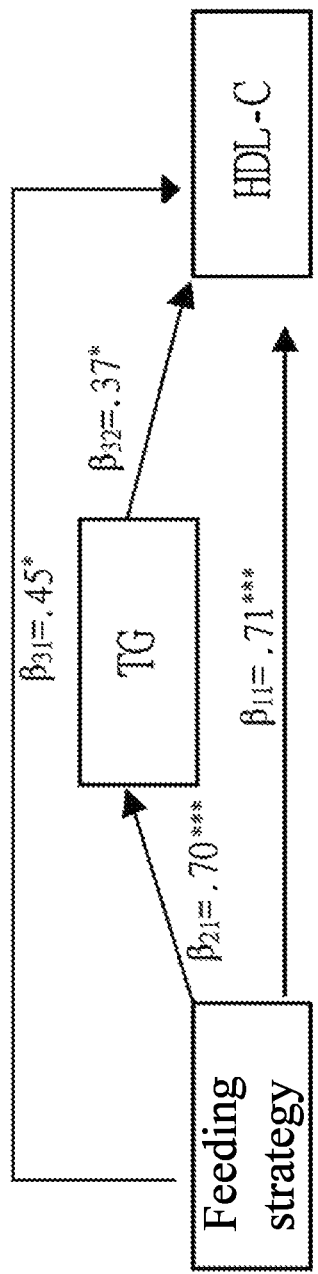

Referring to FIG. 7, TG has a partial mediation effect on the effect of feeding strategies on HDL.

Figure 8:
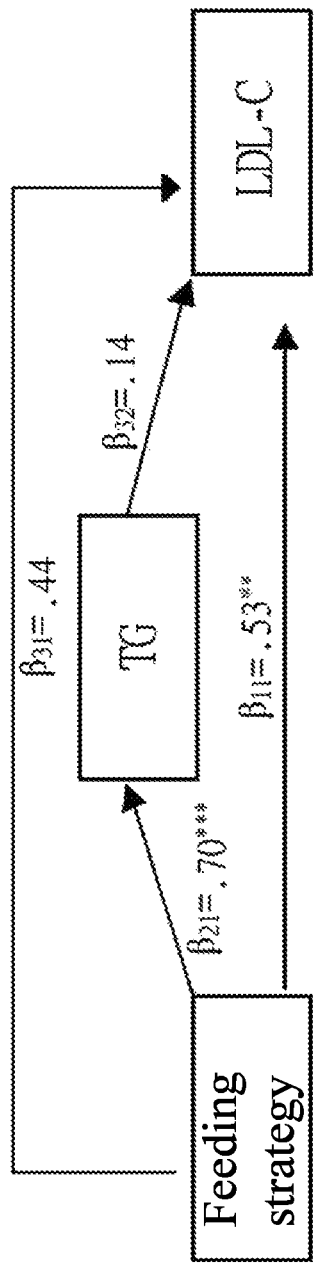

Referring to FIG. 8, TG has no mediation effect on the effect of feeding strategies on LDL.

Figure 9:
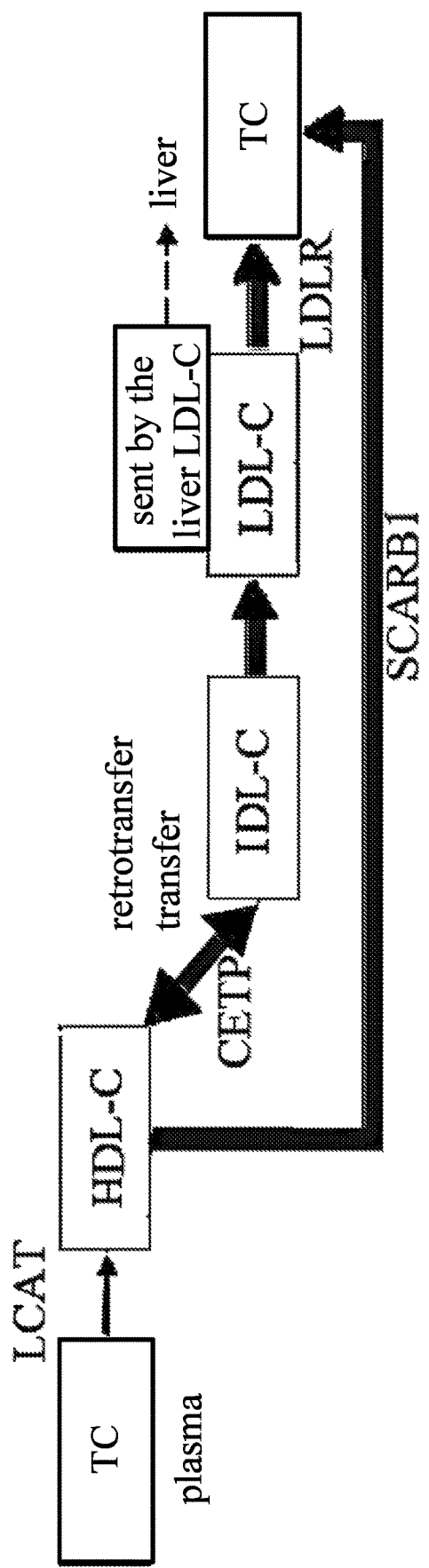
FIGS. 9 to 11 are schematic diagrams of lipoprotein and lipid metabolism relationship established by lipoprotein-lipid complex of the herbal formula of the present disclosure.
Figure 10:
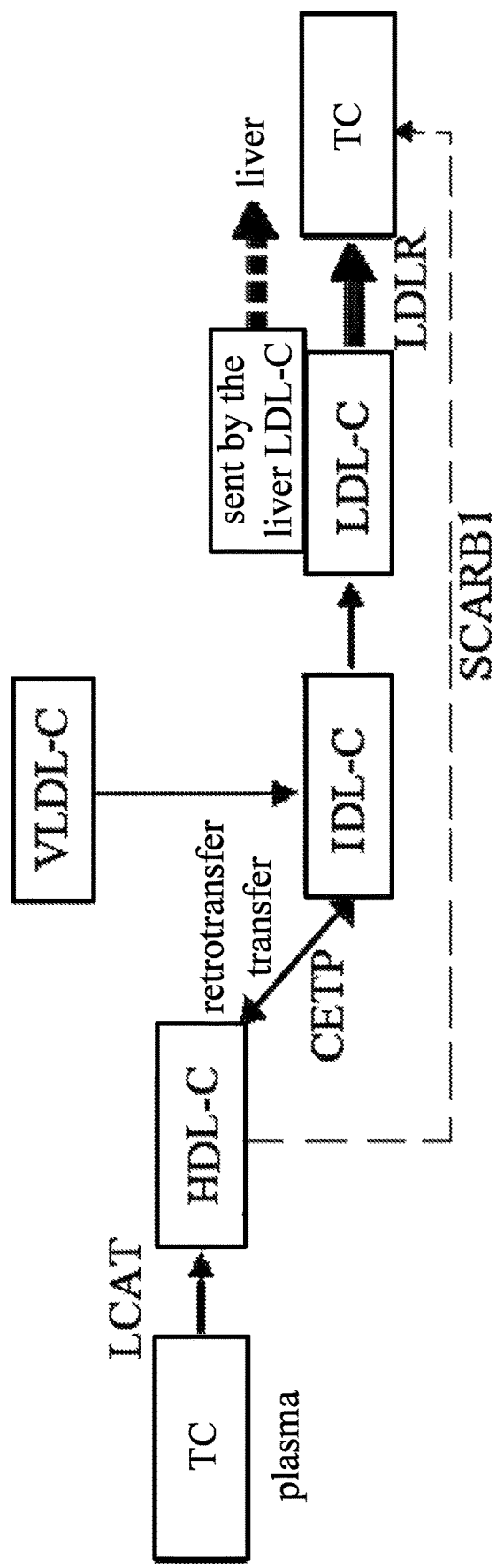
Figure 11:
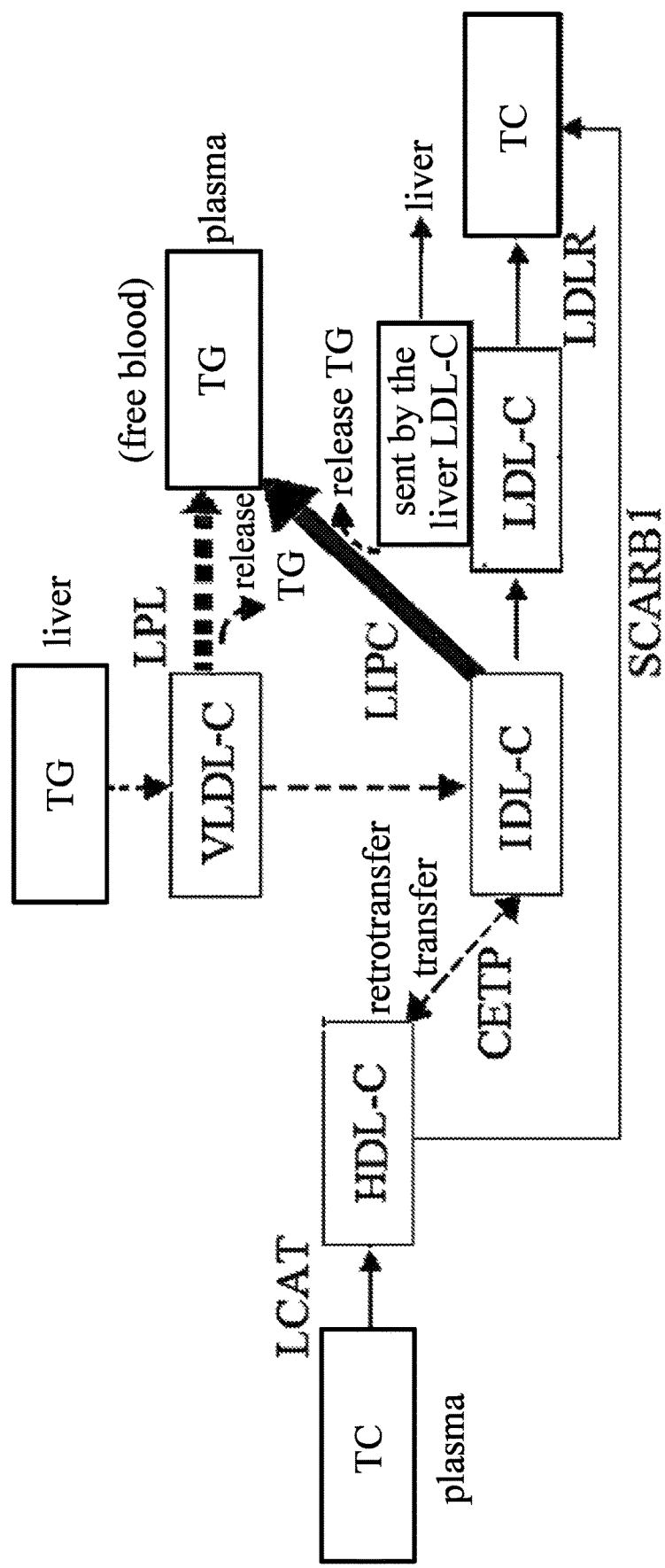

Referring to FIG. 9 to FIG. 11, the lipoprotein and lipid simultaneous group sets up a lipoprotein and lipid metabolism map, referred to as lipoprotein and lipid metabolism map.

FIG. 9 shows the effect between HDL-C and TC, FIG. 10 shows the effect between LDL-C and TC, and FIG. 11 shows the effect between HDL-C and TG and between LDL-C and TG.

The lipoprotein and lipid metabolism maps are referenced together with the multiple regression mediations.

FIG. 9 shows the lipoprotein and lipid metabolism map between HDL-C and TC, and FIG. 1 and FIG. 5 show the effect between HDL-C and TC.

FIG. 10 shows the lipoprotein and lipid metabolism map between LDL-C and TC, and FIG. 3 and FIG. 6 show the effect between LDL-C and TC.

FIG. 11 shows the lipoprotein and lipid metabolism map between HDL-C and TG, and FIG. 2 and FIG. 7 show the effect between HDL-C and TG.

FIG. 11 shows the lipoprotein and lipid metabolism map between LDL-C and TG, and FIG. 4 and FIG. 8 show the effect between LDL-C and TG.

FIG. 1 shows the effect of HDL-C on TC, the feeding strategy improves the effect on TC, and the direct effect is 0.07, the indirect effect is 0.65, and the total effect is 0.72.

FIG. 2 shows the effect of HDL-C on TG, the feeding strategy improves the effect on TG, and the direct effect is 0.43, the indirect effect is 0.27, and the total effect is 0.70.

FIG. 3 shows the effect of LDL-C on TC, the feeding strategy improves the effect on TC, and the direct effect is 0.50, the indirect effect is 0.20, and the total effect is 0.71.

FIG. 4 shows the effect of LDL-C on TG, the feeding strategy improves the effect on TG, and the direct effect is 0.65, the indirect effect is 0.05, and the total effect is 0.70.

FIG. 5 shows the effect of TC on HDL-C, the feeding strategy improves the effect on HDL-C, and the direct effect is 0.06, the indirect effect is 0.65, and the total effect is 0.71.

FIG. 6 shows the effect of TC on LDL-C, the feeding strategy improves the effect on LDL-C, and the direct effect is 0.14, the indirect effect is 0.39, and the total effect is 0.53.

FIG. 7 shows the effect of TG on HDL-C, the feeding strategy improves the effect on HDL-C, and the direct effect is 0.45, the indirect effect is 0.26, and the total effect is 0.71.

FIG. 8 shows the effect of TG on LDL-C, the feeding strategy improves the effect on LDL-C, and the direct effect is 0.43, the indirect effect is 0.10, and the total effect is 0.53.

The results show that as to the effect of feeding strategies on TG, TC, and HDL-C, the explanatory power of the coefficient of determination of the mapping relationship is more than 70%, which is significant.

As to the effect of feeding strategies on LDL-C, the explanatory power of the coefficient of determination of the mapping relationship exceeds 50%, and the main difference is in the non-systemic blood.

LDL-C is sent out directly by the liver and enters the liver cells by endocytosis, causing a decrease in explanatory power. Although TC and LDL-C are proportional between the basic group, the low-dose group and the control group, the high-dose group, the high-dose group and the low-dose group, especially the high-dose group, inhibits liver cholesterol synthesis and increases the number of LDL-receptors in liver cells.

Figure 12:
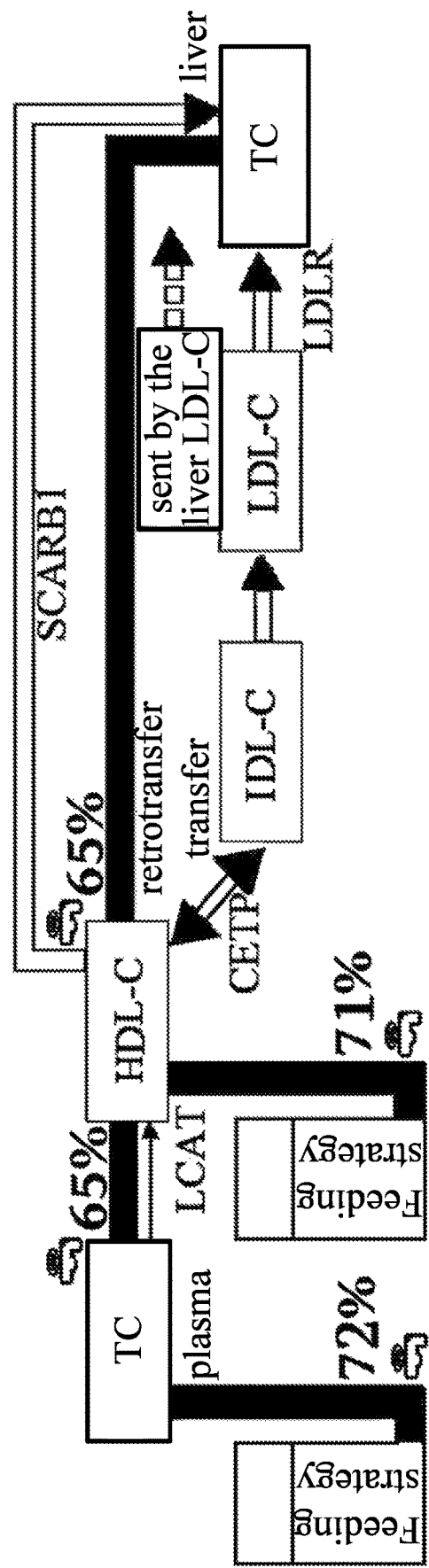
FIGS. 12 to 14 are diagrams of system dynamics established by lipoprotein-lipid complex of the herbal formula of the present disclosure.
Figure 13:
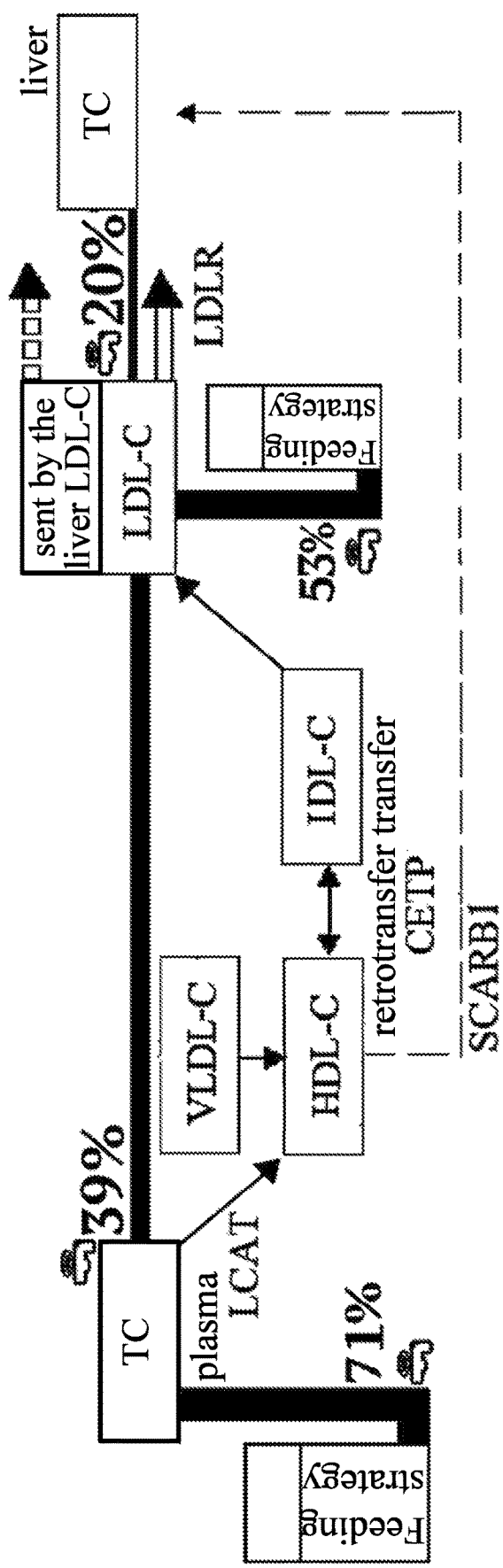
Figure 14:
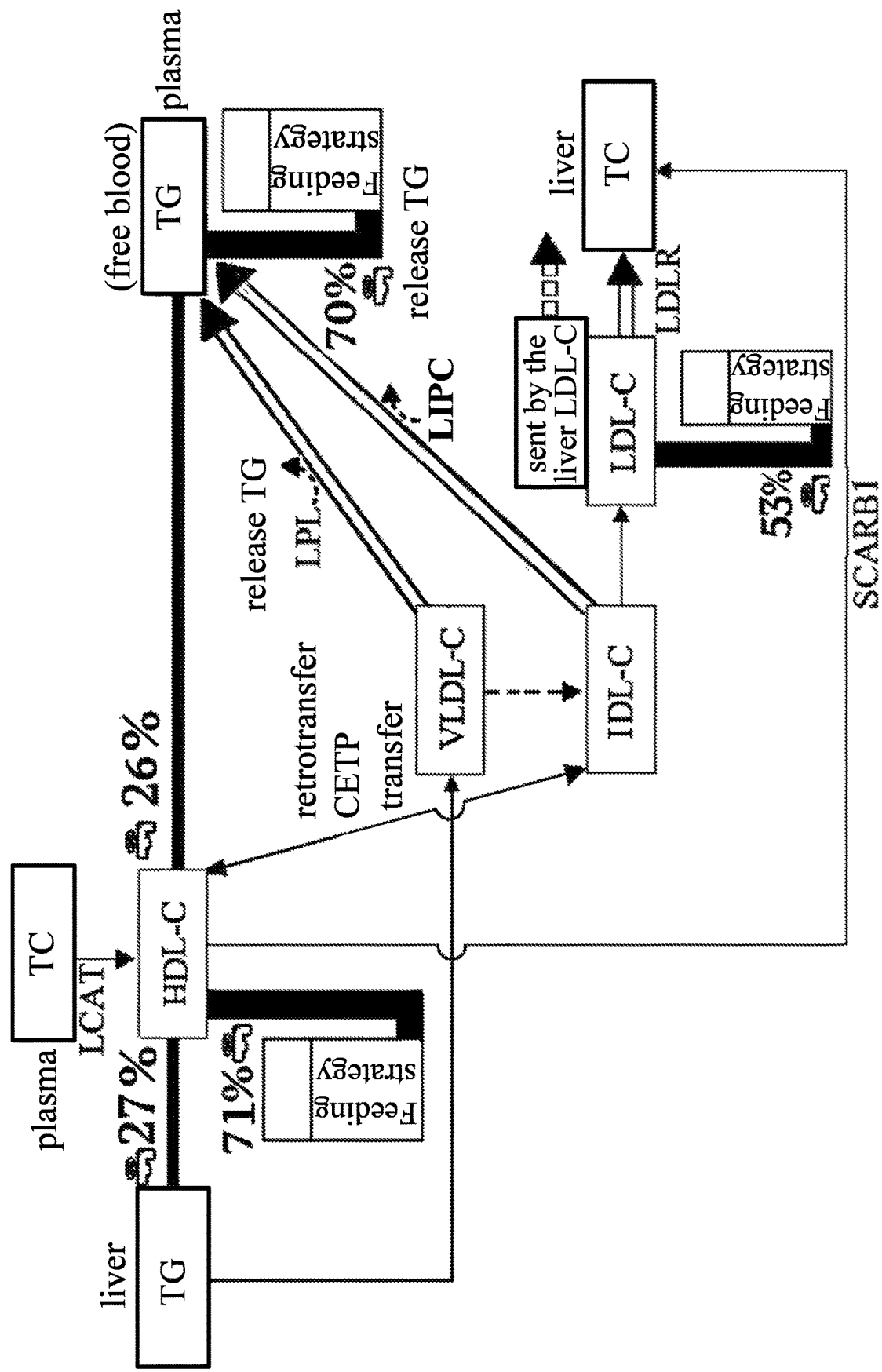

FIGS. 12 to 14 are diagrams of system dynamics established by the simultaneous group of lipoprotein-lipid complex of the herbal formula of the present disclosure.

The following description describes that the relationship between HDL-C and TC metabolism is established.

Referring to FIG. 5, the feeding strategy has an explanatory power of 0.71* on HDL-C, and TC has a complete mediating effect on HDL-C in the feeding strategy ($\beta_{32}$ value=0.92*). Referring to FIG. 1, the feeding strategy has an explanatory power of 0.72* on TC, and HDL-C has a complete mediating effect on TC in the feeding strategy ($\beta_{32}$ value=0.91*). Referring to FIG. 12, the indirect effects between the above feeding strategies are all 65%. TC has a complete mediating effect on HDL-C in the feeding strategy, and the feeding strategy affects HDL-C indirectly by TC. In the 65% of indirect effect, TC in the plasma has completely mediated HDL-C in the plasma by the lecithin-cholesterol acyltransferase (LCAT) according to the expected index content group ratio.

HDL-C has a complete mediating effect on TC in the feeding strategy, and the feeding strategy affects TC indirectly by HDL-C. In the 65% of indirect effect, HDL-C in the plasma has completely mediated TC in the plasma by scavenger receptor class B member 1 (SCARB1) directly, and by cholesterol ester transfer protein (CETP) transfer HDL-C into intermediate-density lipoprotein (IDL-C) and LDL-C, and then through low-density lipoprotein receptor (LDLR), according to the expected index content group ratio.

The following description describes that the relationship between LDL-C and TC metabolism is established.

Referring to FIG. 6, the feeding strategy has an explanatory power of 0.53** on LDL-C, and TC has a complete mediating effect on LDL-C in the feeding strategy ($\beta_{32}$ value=0.55*). Referring to FIG. 3, the feeding strategy has an explanatory power of 0.71*** on TC, and LDL-C has a partial mediating effect on TC in the feeding strategy ($\beta_{32}$ value=0.38*). Referring to FIG. 13, the indirect effects between the above feeding strategies respectively are 39% and 20%. TC has a complete mediating effect on LDL-C in the feeding strategy, and the indirect effect is 39%. LDL-C has a partial mediating effect on TC in the feeding strategy, and the indirect effect is 20%.

Referring to FIG. 10, TC in the plasma has the following three pathways. One is that TC enters HDL-C via LCAT and then converts into IDL-C through CETP so as to enter LDL-C, and another is that TC enters HDL-C via LCAT and then is sent into liver directly via SCARB1, and the other is that LDL-C is sent into liver directly.

Referring to FIG. 10, LDL-C in the plasma has the following three pathways. One is that LDL-C is sent directly through the liver, another is that LDL-C directly enters HDL-C via LCAT, and then indirectly converts to IDL-C and LCL-C then passes through LDLR, and the other is that LDL-C is directly transmitted to IDL-C and LDL-C via very-low-density lipoprotein (VLDL-C) and then through LDLR.

Referring to FIG. 13, TC has a complete mediating effect on LDL-C in the feeding strategy. In 39% of the indirect effect, TC in the plasma effects LDL-C in the plasma, the liver cholesterol is transported to surrounding tissues, and TC is completely mediated into LDL-C according to the expected index content group ratio.

LDL-C has a partial mediating effect on TC in the feeding strategy. In 20% of the indirect effect, LDL-C in the plasma effects TC in the plasma, cholesterol-rich LDL-C is partially mediated by the expected index content group ratio, and it is sent away to cholesterol TC in the plasma flowing through the liver.

The following description describes that the relationship between HDL-C and TG metabolism is established.

Referring to FIG. 7, the feeding strategy has an explanatory power of 0.71*** on HDL-C, and TG has a partial mediating effect on HDL-C in the feeding strategy ($\beta_{32}$ value=0.37*). Referring to FIG. 2, the feeding strategy has an explanatory power of 0.70*** on TG, and HDL-C has a partial mediating effect on TG in the feeding strategy ($\beta_{32}$ value=0.38*).

Referring to FIG. 14, the indirect effects between the above feeding strategies respectively are 27% and 26%. TG has a partial mediating effect on HDL-C in the feeding strategy, and the indirect effect is 27%. HDL-C has a partial mediating effect on TG in the feeding strategy, and the indirect effect is 26%.

Referring to FIG. 11, TG in the plasma releases triglycerides into the blood through the following three pathways. One is that TG pass through the lipoproteinlipase (LPL) by VLDL-C, and another is that TG is transmitted through LPL via VLDL-C and then directly being transmitted to IDL-C through hepatic lipase (LIPC), and the other is that TG is transmitted through LPL via VLDL-C and then transferred to IDL-C and then exchanged HDL-C through CETP and then converted to IDL-C through LIPC.

Referring to FIG. 11, HDL-C in the plasma releases triglycerides into the blood through the following two pathways. One is that HDL-C directly passes through by SCARB1, and the other is that HDL-C is converted into IDL-C and LDL-C indirectly via CETP and then through LDLR.

Referring to FIG. 14, TG has a partial mediating effect on HDL-C in the feeding strategy. In 27% of the indirectly effect, TG in the plasma has a mediating effect on HDL-C, TG released in the blood are partially mediated by HDL-C in the blood according to the expected index content group ratio. HDL-C has a partial mediating effect on TG in the feeding strategy. In 26% of the indirect effect, the HDL-C in the plasma has a mediating effect on TG, HDL-C released in the blood are partially mediated by TG in the blood according to the expected index content group ratio.

The following description describes the relationship between LDL-C and TG metabolism being unable to be established.

Referring to FIG. 8, the feeding strategy has an explanatory power of 0.53** on LDL-C, and TG has no mediating effect on LDL-C in the feeding strategy ($\beta_{32}$ value=0.14).

Referring to FIG. 4, the feeding strategy has an explanatory power of 0.70*** on TG, and LDL-C has no mediating effect on TG in the feeding strategy ($\beta_{32}$ value=0.10).

The indirect effects between the above feeding strategies respectively are 10% and 5% (data is not shown).

Referring to FIG. 11, TG in the plasma releases triglycerides into the blood through the following three pathways. One is that TG passes through the lipoproteinlipase (LPL) by VLDL-C, and another is that TG is transmitted through LPL via VLDL-C and then directly being transmitted to IDL-C through LIPC, and the other is that TG is transmitted through LPL via VLDL-C and then transfer to IDL-C and then exchange HDL-C through CETP and then convert to IDL-C through LIPC.

Referring to FIG. 11, LDL-C in the plasma has the following three pathways. One is that LDL-C is sent directly through the liver, another is that LDL-C directly enters HDL-C via LCAT, and then indirectly converts to IDL-C and LCL-C then pass through LDLR, and the other is that LDL-C is directly transmitted to IDL-C and LDL-C via VLDL-C and then through LDLR.

Referring to FIG. 14, TC has no mediating effect on LDL-C in the feeding strategy. In 10% of the indirect effect, TC in the plasma dose not effect LDL-C in the plasma, TC in the blood did not release the LDL-C in the blood according to the expected index content group ratio.

LDL-C has no mediating effect on TC in the feeding strategy. In 5% of the indirect effect, LDL-C in the plasma dose not effect TC in the plasma, LDL-C in the blood did not release the TG in the blood according to the expected index content group ratio.

FIG. 9 includes the metabolism of HDL-C and TC, which is marked with a thin-line arrow, and TC has a complete mediating effect and completely enters HDL-C; and the direction that CETP converts is marked with a thick-double arrow, HDL-C has a complete mediating effect on TC in the feeding strategy, the higher the concentration of HDL-C, the more TC being sent away.

FIG. 10 includes the metabolism of LDL-C and TC, which is marked with thin-line arrows and a thin dotted arrow, and TC has a complete mediating effect on LDL-C, the lower the concentration of TC is, the lower the concentration of LDL-C is; and LDL-C has a partial mediating effect on TC, which is marked with a thick-line arrow and a thick dotted arrow, enters the liver cells by endocytosis to send away TC in the blood through the liver. In summary, the thin-line arrows and the thick-line arrow shows TC decreases according to the expected index content group ratio. Both of them create the high and low doses of the herbal formula, especially the high dose, inhibit liver cholesterol synthesis, and increase the number of liver cell LDLR.

FIG. 11 includes the metabolism of HDL-C and TG, which is marked with thin dotted arrows, the direction that CETP converts is marked with a thin dotted arrow, and TG has a partial mediating effect on HDL-C, which is marked with a thick-line arrow and a thick dotted arrow, that part of TG released in the blood is mediated by HDL-C in the blood; the direction that CETP converts is marked with a thin dotted arrow and the SCARB1 is marked with a thin-line arrow, so that HDL-C has a partial mediating effect on TC, and part of TG released in the blood is mediated by HDL-C in the blood. In summary, compared with the control group, the high and low doses of the herbal formula inhibit CETP exchange, the high dose of the herbal formula is slightly stronger, can reduce the exchange of HDL-C and reduce the release of TG from the blood.

FIG. 11 includes that the metabolism of LDL-C and TG cannot be established and failed to mark the mediating effect of LDL-C and TG. TG has no mediating effect on LDL-C in the feeding strategy. TG released in the blood is not mediated by LDL-C in the blood. LDL-C has no mediating effect on TC in the feeding strategy. TG released in the blood is not mediated by LDL-C in the blood. LDL-C in the blood does not mediate the release of TG into the blood.

Figure 15:
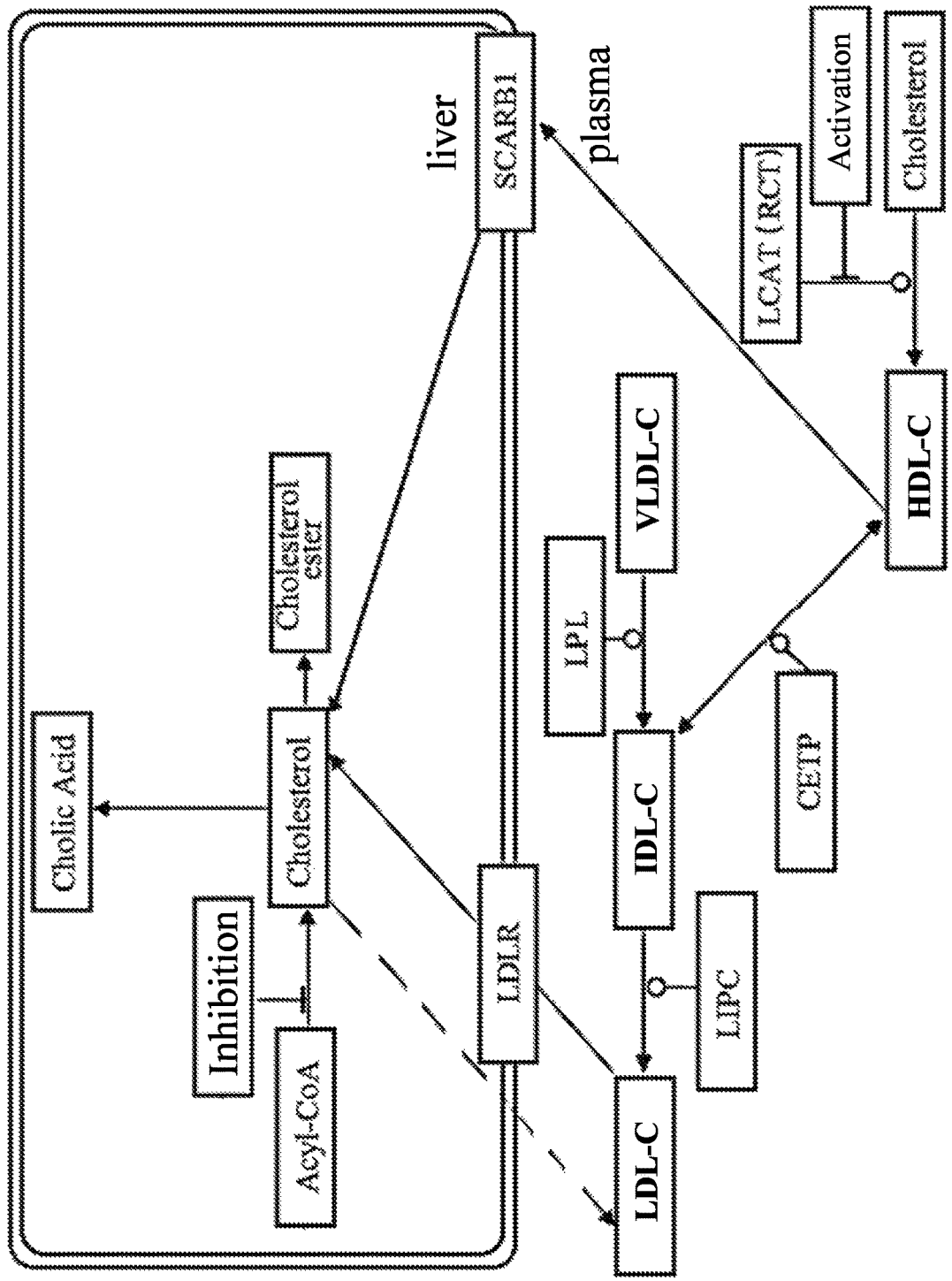
FIG. 15 and FIG. 16 are diagrams of the interaction path of blood lipid metabolism depicted by the comparison between the herbal formula metabolism and cholesterol drug metabolism.
Figure 16:
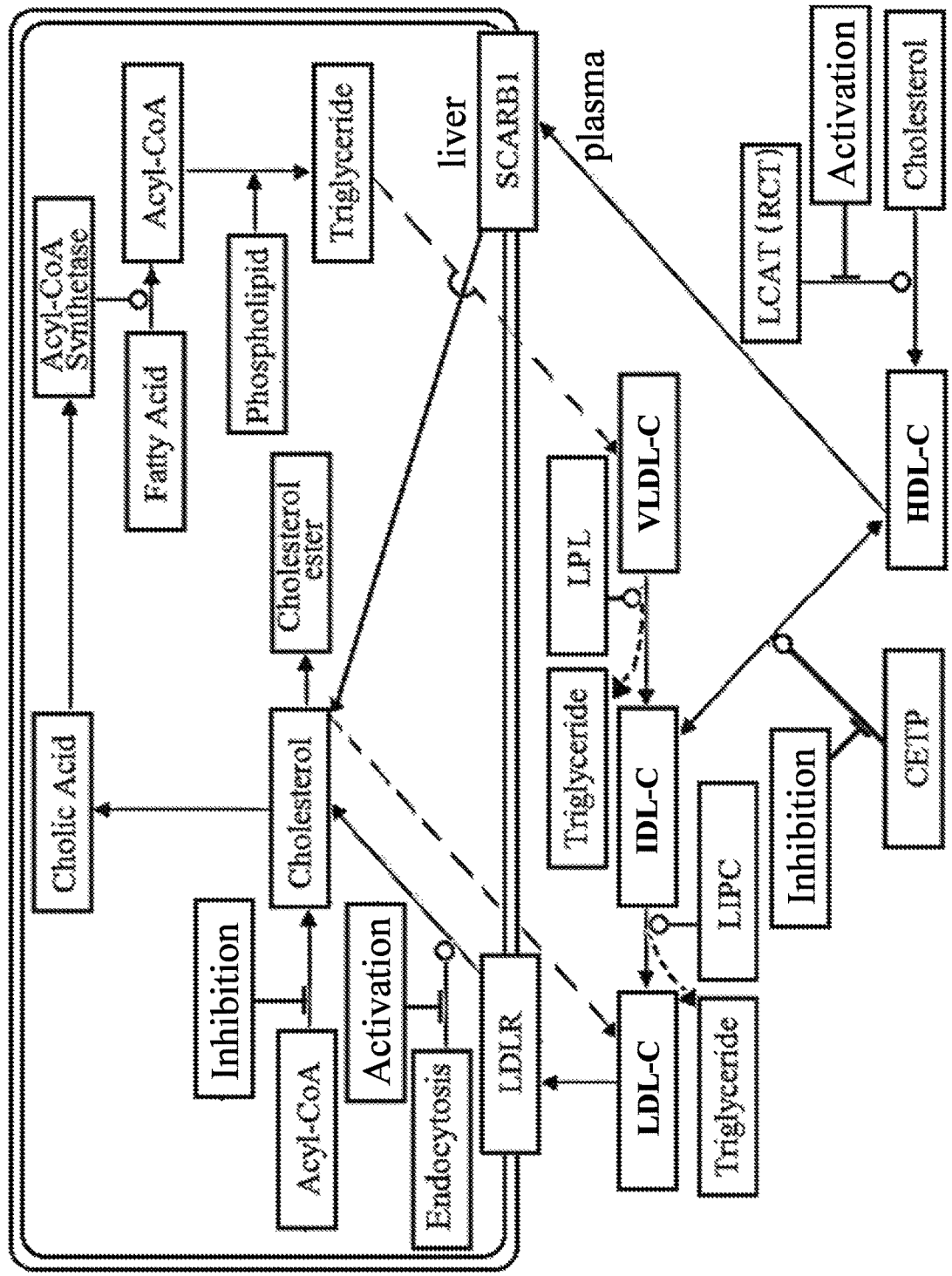

Referring to FIGS. 15 and 16 which are diagrams of the interaction path of blood lipid metabolism depicted by the comparison between the herbal formula metabolism and cholesterol drug metabolism. HMG-CoA reductase inhibitor mainly reduces the concentration of cholesterol and even reduces the concentration of LDL-C (by inhibiting liver cholesterol synthesis and increasing the number of LDL-receptors in liver cells). CETP inhibitor is a molecule that transfers cholesterol between HDL-C and LDL-C, CETP transfers cholesterol between HDL-C and LDL-C. Therefore, when the activity of CETP is inhibited and reduced, HDL-C will increase (or based on HDL-C/TG), LDL-C will decrease, and the less HDL-C is exchanged, the less TG is released from the blood.

The comparison of cholesterol drug metabolism is shown as FIG. 15. The high-dose and low-dose ratios can be used to compare the metabolic relationship between the multiple cargos and the multiple carriers. In the corrected descriptive statistics table, the ratio values of the four groups of the basic group, the control group, the low dose and the high dose group, "h" represents approximately equal to. TG≈1:4:2.0:1.9. TC≈1:4.0:2.4:2.0. HDL-C≈1:4:2.7:2.2. LDL-C≈1:4.0:2.4:0.2. HDL-C/TG≈1:0:1.0:1.0.

Figure 17:
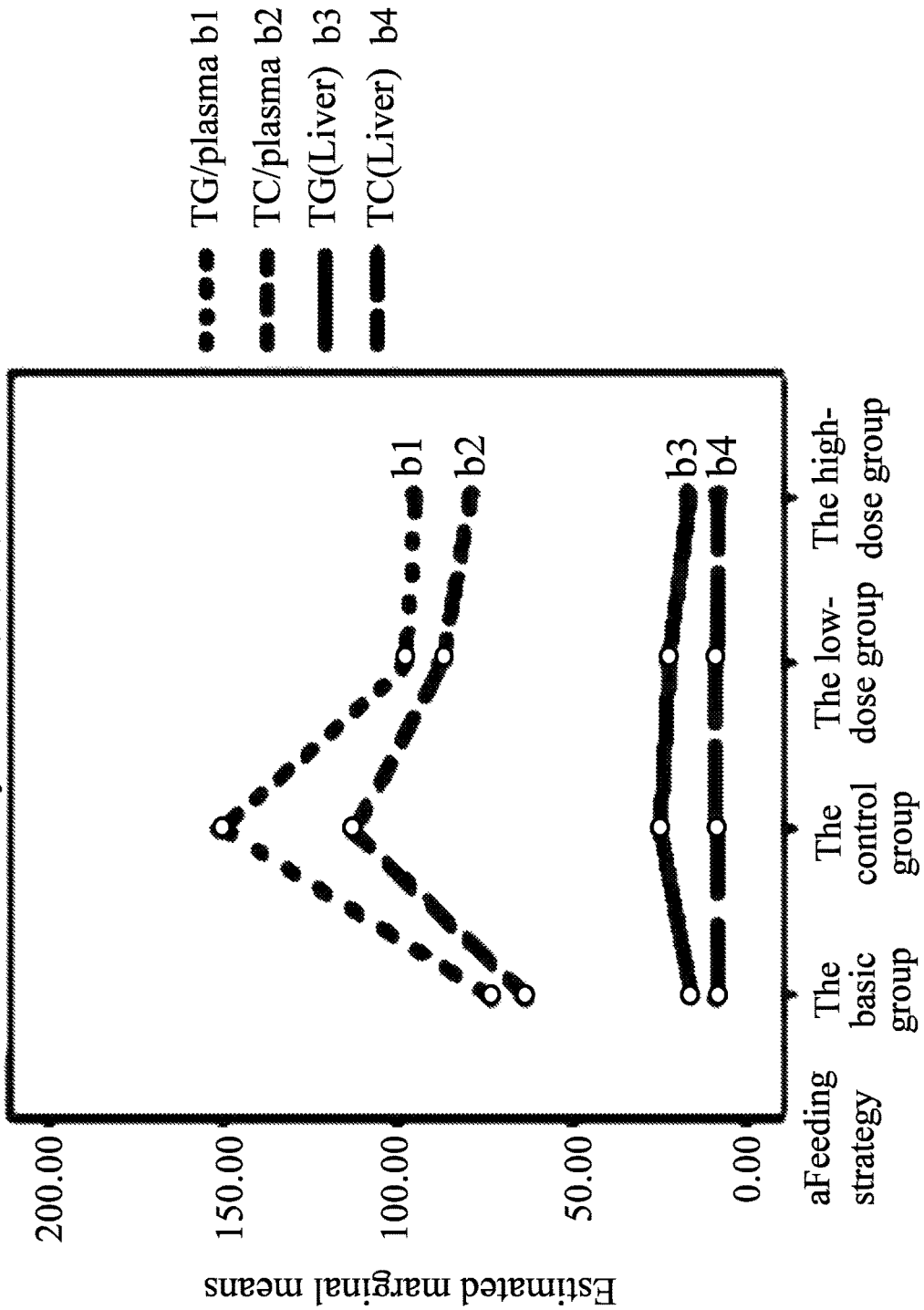
FIG. 17 and FIG. 18 are comparison diagrams of post-mortem analysis of two-factor mixed-design analysis of variance for the herbal formula of the present disclosure.
Figure 18:
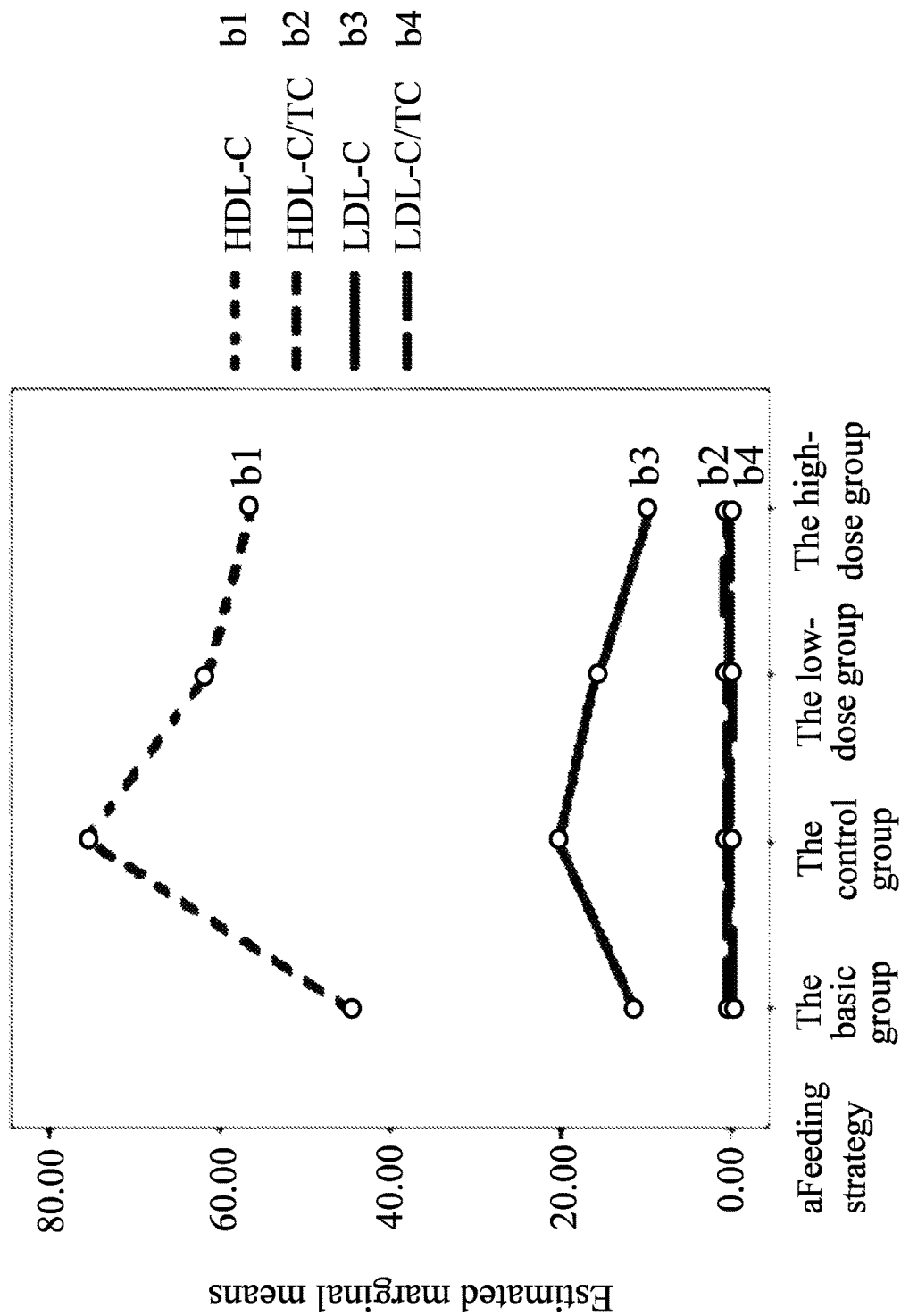

FIG. 17 and FIG. 18 are comparison diagrams of post-mortem analysis of two-factor mixed-design analysis of variance for the herbal formula of the present disclosure, which establishes lipoprotein and lipid simultaneous groups. In FIG. 17, TG/plasma and TC/plasma are significantly different, but TG(liver) and TC(liver) are not significantly different. In FIG. 18, TG/plasma and LDL-C are significantly different, but HDL-C/TC and LDL-C/TC are not significantly different.

Referring FIG. 17, the feeding strategy of TG in the comparison diagrams of post-mortem analysis, triglyceride-≈the low dose group* # and the high dose group* #. The conclusion is that the metabolism of high-dose and low-dose cholesterol drugs is reduced compared with the control group, but the high-dose and low-dose cholesterol are both effective and not much different.

The feeding strategy of TC in the comparison diagrams of post-mortem analysis, cholesterol≈the low dose group* # and the high dose group #. The conclusion is that both high-dose and low-dose cholesterol drugs are effective for metabolism, and the high-dose cholesterol drug is more effective and closer to rehabilitation.

Referring FIG. 18, the feeding strategy of HDL-C in the comparison diagrams of post-mortem analysis, HDL-C≈the low dose group* # and the high dose group* #. The conclusion is that the metabolism of high-dose and low-dose cholesterol drugs is significantly increased compared to the basic group, and both high- and low-dose groups are effective and not much different. In the chart, the HDL-C/TG ratio of the control group, the high dose group and the low dose group are essentially the same, and the HDL-C/TG ratio of the basic group is very low.

The feeding strategy of LDL-C in the comparison diagrams of post-mortem analysis, LDL-C≈the low dose group (blank) and the high dose group* #. The conclusion is that high-dose cholesterol drugs are very effective in reducing TC, and it also causes LDL-C metabolism to be particularly effective and has significant differences from the control group. The low-dose group is effective for reducing LDL-C but there is no significant difference between the basic group and the control group. On the contrary, the low-dose group of the cholesterol drug is better than the expected index content for reducing TC.

Compared with cholesterol drug metabolism, methods to effectively improve cholesterol metabolism include the feeding strategies to indirectly explain HDL-C through TC. High and low doses of the cholesterol drug metabolism is effective for TC, and high dose of the cholesterol drug is more effective for TC and closer to cure, the greater the dose is, the greater the total effect increases. However, the marginal effect gradually decreases. TC highly interprets HDL-C indirectly during the obvious improvement process. LCAT converts cholesterol into cholesterol ester and transfers it to the center of cholesterol-free lipoprotein to form HDL-C. The feeding strategies indirectly explain TC through HDL-C. The metabolism of cholesterol in the high-dose and the low-dose cholesterol groups is significantly different from that in the basic group, but both high- and low-dose groups of cholesterol are effective and the difference is not significant. In the chart, HDL-C/TG ratio in the basic group, high-dose group, and low-dose group are essentially the same, and the control group has a low HDL-C/TG ratio. HDL-C explains TC in a highly indirect way during the process of obvious improvement. Reverse cholesterol transport (RCT) of cholesterol transports TC in the blood through HDL-C via SCARB1, HDL-C, and cholesterol is excreted out of the body in the form of cholic acid.

The feeding strategies indirectly explain LDL-C through TC. Cholesterol drug metabolism in both the high-dose group and the low-dose group is effective for TC, and the high-dose group is more effective and closer to cure for TC. The higher the dose is, the greater the overall effect increases. However, the marginal effect gradually decreases, and it also causes LDL-C metabolism to be particularly effective and has a significant difference from the control group, and TC slightly highly indirectly explains LDL-C, obviously in the process of improvement. 60-70% of cholesterol in the blood is carried by low-density lipoprotein cholesterol, the lower the TC concentration is, the much lower the LDL-C concentration is.

The feeding strategies indirectly explain TC through LDL-C. The high-dose group is particularly effective for lowering LDL-C and lower than the other three groups. The low-dose group is effective and lower than the control group and the basic group but there is no significant difference between the three groups. LDL-C moderately indirectly explains TC, and during the very obvious improvement process, LDL-C enters liver cells by combining with LDLR and via endocytosis.

The therapeutic effects described in the present disclosure is that, by comparing cholesterol drug metabolism, the high and low dose groups effectively improved the metabolic relationship between cholesterol and high and low density lipoprotein cholesterol. In addition, the low-dose group is effective in improving cholesterol metabolism compared to cholesterol drug metabolism.

FIG. 16 depicts the path of blood fat metabolism interaction. In this way, the high-dose group and the low-dose group can describe the effectiveness of multiple carrier polymer metabolism interaction pathways. Compared with the control group, the high-dose group and the low-dose group significantly reduced triglycerides. The high-dose group and the low-dose group have similar triglyceride content, and both of them are higher than the basic group and are lower than the control group. The high-dose group is slightly better for cholesterol-improving and triglyceride-improving according to the desired index content ratio.

Compared with the basic group, the high-dose group and the low-dose group have a significant difference in increasing HDL-C, according to HDL-C increased (or based on HDL-C/TG). Compared with the control group, the high-dose group and the low-dose group have a significant difference in reducing HDL-C, and while the high-dose group and the low-dose group are effective in improving cholesterol, there is not much difference in the effectiveness. The HDL-C/TG ratio in the basic group, the high-dose group and the low-dose group are essentially the same. The control group contains a very low HDL-C/TG ratio; low HDL-C and high TG, low HDL-C/TG ratio, and a strong response to abdominal fat in particular. Therefore, the high-dose cholesterol drugs are relatively effective for reducing abdominal fat, and are also effective in weight loss and are significantly different from the control group; the low-dose cholesterol drugs are effective in reducing abdominal fat but there is no significant difference between the basic group and the control group.

Therefore, the way to describe the pathway of blood fat metabolism interaction to effectively improve cholesterol and triglyceride metabolism is that the interaction pathway of blood fat metabolism is mainly through the inhibition of inhibitors, and the activation of enzymes or receptors, which includes reducing cholesterol synthesis through HMG-CoA reductase inhibitors and lowering TC and LDL-C concentrations during the improvement process. Through the RCT of cholesterol, LCAT allows HDL-C to send away TC in the blood through transesterification reaction. Cholesterol is excreted out of the human body in the form of cholic acid during the process of improvement, so as to reduce TC concentration. LDL-C enters liver cells by combining with LDLR and via endocytosis during the process of improvement, so as to reduce LDL-C concentration.

The herbal formula of the present disclosure inhibits the function of CETP by CETP inhibitor. During the process of improvement, the exchange of HDL-C is reduced, the release of TG in the blood is reduced, and the production of HDL-C is also reduced. HDL-C increases and decreases LDL-C concentration. HDL-C increases and sends away TC in the blood. The much lower the TC concentration is, the lower the LDL-C concentration is.

Compared with the basic group, HDL-C increased in the high-dose group and the low-dose group. The HDL-C/TG ratio in the basic group, high-dose group, and low-dose group in the chart are essentially the same, the HDL-C/TG of the control group is very low.

The therapeutic effect described in the present disclosure is that, according to the interaction inhibition and activation pathways of blood fat metabolism, the high and low dose groups effectively improve cholesterol and triglyceride metabolism. The high-dose group effectively improves cholesterol and triglyceride metabolism according to the pathway of blood fat metabolism interaction. The low-dose group effectively improves cholesterol and triglyceride metabolism according to the pathway of blood fat metabolism interaction.

β regression coefficient is mainly used to determine HMG-CoA reductase inhibitor, to verify the explanatory power of coefficients and the explanatory power of intermediary effects with the mapping relationship of β regression coefficients as variables.

Referring to FIGS. 12 to 14 and Table. 2, the explanatory power of the statistical model of the coefficient of determination of the mapping relationship and the explanatory power of the mediation effect, after adding the total effect and indirect effect to the regression intermediary map, the percentage (%) of the diameter of the thick black pipeline in the figures are used as the explanatory power.

First, the following description describes LDL-C in the feeding strategy is determined.

The explanatory power of the statistical model is shown in Table 2, TC≈1:4.0:2.4:2.0, LDL-C≈1:4.0:2.4:0.2. The feeding strategy has an explanatory power of 0.71* on TC (as marked 71% in FIG. 13). The feeding strategy has an explanatory power of 0.53 on LDL-C (as marked 53% in FIG. 13). The explanatory power of the LDL-C determination coefficient is reduced by 18% compared with TC, which indicates that the ratio of the basic group, control group, and low-dose group LDL-C is equal to TC. However, LDL-C≈0.2 in the high-dose group is better than TC≈2.0, the explanatory power of LDL-C in the feeding strategies is weak, and the weaker the coefficient of determination becomes, the better the therapeutic effect is, even better than that expected in the high-dose group. The amount of LDL-C in the upper and lower pathway of the high-dose group decreased more than the expected index content group ratio decreased.

The following description describes the explanatory power of the mediation effect. TC has an indirect effect on LDL-C in the feeding strategy, which is 39%. LDL-C has an indirect effect on TC in the feeding strategy, which is 20%. The feeding strategy has less ability to explain TC indirectly through LDL-C, and the indirect effect is particularly low. LDL-C enters the liver cells by endocytosis, and more LDL-C will send away TC in the blood through the liver. The low indirect effects make treatment effects particularly better, and the high-dose group and the low-dose group reduce LDL-C concentration, especially LDL-C≈0.2 in the high-dose group. HMG-CoA reductase inhibitors mainly reduce the concentration of LDL-C, and the influence of β regression coefficient can confirm that the high-dose group and low-dose group accord with the characteristics of HMG-CoA reductase inhibitor.

Second, the following description describes how TC in the feeding strategy is determined.

The following description describes the explanatory power of the mediation effect. The feeding strategy has an explanatory power of 0.71*** on TC (as marked 71% in FIG. 13).

The high-dose and the low-dose groups of the cholesterol drug metabolism is effective for TC, and high dose of the cholesterol drug is more effective for TC and closer to cure, the greater the dose is, the greater the total effect increases. However, the marginal effect gradually decreases. The feeding strategy has a great ability to explain TC, the coefficient of determination is enormously powerful, has only slightly better than the expected therapeutic effect, and even the low-dose group doses are greater than the expectation.

The following description describes the explanatory power of the mediation effect. TC has an indirect effect on LDL-C in the feeding strategy, which is 39%. TC has a strong explanatory power of mediation effect on LDL-C in the feeding strategy that is better than the expectation. The lower the TC concentration is, the lower the LDL-C concentration is. The high-dose group and the low-dose group reduce TC concentration, especially TC 2.4 in the low-dose group. HMG-CoA reductase inhibitors mainly reduce the concentration of TC, and the influence of β regression coefficient can confirm that the high-dose group and low-dose group accord with the characteristics of HMG-CoA reductase inhibitor.

The direction of the regression path mainly determines CETP inhibitors, carrier-polymer relationship using regression path directionality as a variable and removing carrier-polymer relationship for verification.

Referring to FIGS. 12 to 14 and Table. 2, use the thick black pipeline in the figure from left to right and bottom to top as the explanatory power of the direction of the regression path, and map the system dynamics according to the mapping function The cargo passes through the carrier and has the relationship of a carrier polymer. The thick black pipeline on the left of the carrier is the cargo entering the carrier, and the thick black pipeline on the right of the carrier is the carrier sending the cargo away.

In FIG. 12, the directionality of TC cargo and HDL-C carrier includes TC being completely mediated into HDL-C through LCAT according to the expected index content group ratio, and HDL-C being completely mediated into TC in the blood according to the expected index content group ratio.

In FIG. 13, the directionality of TC cargo and LDL-C carrier includes TC being completely mediated into LDL-C according to expected index content group ratio, and LDL-C being partially mediated into mediating sends TC in the blood through the liver according to expected index content group ratio.

FIG. 12 and FIG. 13 have the relationship of carrier polymer to determine the explanatory power of the direction of the regression path. Referring FIG. 18, the feeding strategy of HDL-C in the comparison diagrams of post-mortem analysis, HDL-C the low dose group* # and the high dose group* #. Referring to Table. 2, TG≈1:4:2.0:1.9. TC≈1:4.0:2.4:2.0. HDL-C≈1:4:2.7:2.2. LDL-C≈1:4.0:2.4:0.2. HDL-C/TG≈1:0:1.0:1.0. In addition, inhibition of CETP causes lower HDL-C to be exchanged and also reduces HDL-C to generate LDL-C Inhibition of CETP causes HDL-C to increase and reduces LDL-C concentration. HDL-C increase will send away TC in the blood and consume HDL-C.

Referring FIG. 18, the feeding strategy of HDL-C in the comparison diagrams of post-mortem analysis, compared with the control group, the high-dose group and the low-dose group had a significant difference in reducing HDL-C. The basic group, the low-dose group and the high-dose group have higher HDL-C/TG ratio than the control group. The low-dose group and the high-dose group improve HDL-C concentration compared with the basic group, and improve HDL-C/TC concentration compared with the control group. The influence of the direction of the regression path can prove that the high-dose group and the low-dose group meet the characteristics of CETP inhibitor. Determining the decoupling relationship based on the system dynamics map of mapping function mapping relationship, TG is removed in the carrier coupling relationship.

The carrier releases the cargo and removes the carrier polymer relationship. The thick black pipeline on the left of the carrier is that the cargo comes from the carrier, and the thick black pipeline on the right of the carrier is that the carrier releases the cargo.

In FIG. 14, the directionality of TG cargo and HDL-C carrier includes that TG released in the blood is partially mediated by HDL-C in the blood according to the expected index content group ratio.

Referring FIG. 17, the feeding strategy of TG in the comparison diagrams of post-mortem analysis, TG the low dose group* # and the high dose group* #. Therefore, the descriptive statistics stated that the partial mediating comes from the highest concentration of HDL-C and TG in the control group and the lowest concentration in the basic group. The concentration of the high-dose group and the low-dose group is between the control group and the basic group. Between HDL-C and TG, there are two sets of different rules and ratios in the high-dose group and the low-dose group. TG concentration has reached the therapeutic effect in the low-dose group and has no difference with the concentration in the high-dose group. The interaction between HDL-C and TG becomes lower ($\beta_{32}$ values=0.38* and 0.37*, and $\beta_{11}$ values=0.71* and 0.70*, which are similar), and are generated partial mediating between each other. Inhibition of CETP causes HDL-C to increase and reduces LDL-C being released to the blood. Compared with the control group, the high-dose group and the low-dose group had a significant difference in reducing TC. The therapeutic effect described in the present disclosure is that the influence of the direction of the regression path can prove that the high-dose group and the low-dose group meet the characteristics of CETP inhibitor.

Third Embodiment

The descriptive statistics, independent sample t-test, regression mediation, the establishment of lipoproteins and lipid metabolism, the comparison of cholesterol drug metabolism and depicting the path of blood fat metabolism interaction, and the system dynamics of protein and lipid polymer simultaneous groups of Longan flower water extract and ethyl acetate fraction are performed to compare with the effect of the Longan flower extracts.

Longan flower extract basic group (B) and control group (C) are the same as (B) and (C) of the herbal formula of the second embodiment. The high-dose group (H) is fed with normal commercial feed supplemented with 60% fructose, 250 mg/ml/kg b.w. of the Longan flower water extract. The low-dose group (L) is fed with normal commercial feed supplemented with 60% fructose, 36.3 mg/ml/kg b.w. of the Longan ethyl acetate fraction (EA fraction).

TABLE 4

Corrected descriptive statistical table of the relevant data results of the Longan flower extracts.

| Items (unit) | (B) | (C) | (L) | (H) | (B) | (C) | (L) | (H) |
|---|---|---|---|---|---|---|---|---|
| TG/plasma (mg/dl) | 75.8 | 287.5 | 153.6 | 124.6 | 1.0 | 4.0 | 2.1 | 1.7 |
| TC/plasma (mg/dl) | 62.9 | 108.8 | 88.9 | 75.6 | 1.0 | 4.0 | 2.7 | 1.8 |
| HDL-C (mg/dL) | 45.7 | 73.5 | 63.2 | 57.5 | 1.0 | 4.0 | 2.9 | 2.3 |
| LDL-C (mg/dL) | 31.8 | 59.4 | 45.0 | 35.6 | 1.0 | 4.0 | 2.4 | 1.4 |
| HDL-C/TC | 0.73 | 0.68 | 0.71 | 0.76 | 1.0 | 0.5 | 0.8 | 1.3 |
| LDL-C/TC | 0.51 | 0.55 | 0.51 | 0.47 | 1.0 | 1.4 | 1.0 | 0.6 |
| HDL-C/TG | 0.60 | 0.26 | 0.41 | 0.46 | 1.0 | −1.3 | −0.3 | 0.1 |

TABLE 5 independent sample t-test table of the relevant data results of the Longan flower extracts.

| Items (unit) | Basic group (B) | Control group (C) | Low-dose group (L) | High-dose group (H) |
|---|---|---|---|---|
| TG/plasma (mg/dl) | 75.8 ± 15.0 | 287.5 ± 128.5* | 153.6 ± 33.1*# | 124.6 ± 25.5*# |
| TC/plasma (mg/dl) | 62.9 ± 11.1 | 108.8 ± 27.9* | 88.9 ± 23.2* | 75.6 ± 17.1# |
| HDL-C (mg/dL) | 45.7 ± 8.1 | 73.5 ± 16.9* | 63.2 ± 14.0* | 57.5 ± 11.6* |
| LDL-C (mg/dL) | 31.8 ± 7.7 | 59.4.5 ± 17.1* | 45.0 ± 14.5 | 35.6 ± 4.4# |

Table 5 is the independent sample t-test table of the relevant data results of the Longan flower extracts. In Table 5, "*" represents a significant difference from the basic group (B), "#" represents a significant difference from the control group (C), and if there is none of the above symbols (blank), it means that there is no significant difference between the groups.

As shown in Table 5, in the item of the triglyceride in plasma of the Longan flower extracts, the low-dose group (L) and the high-dose group (H) are marked as * #. In the item of the cholesterol in plasma, the low-dose group (L) is marked as * and the high-dose group (H) is marked as #. In the item of the HDL-C in the plasma, the low-dose group (L) is marked as * and the high-dose group (H) is marked as *. In the item of the item of LDL-C in the plasma, the low-dose group (L) is blank and the high-dose group (H) is marked as #.

Figure 19:
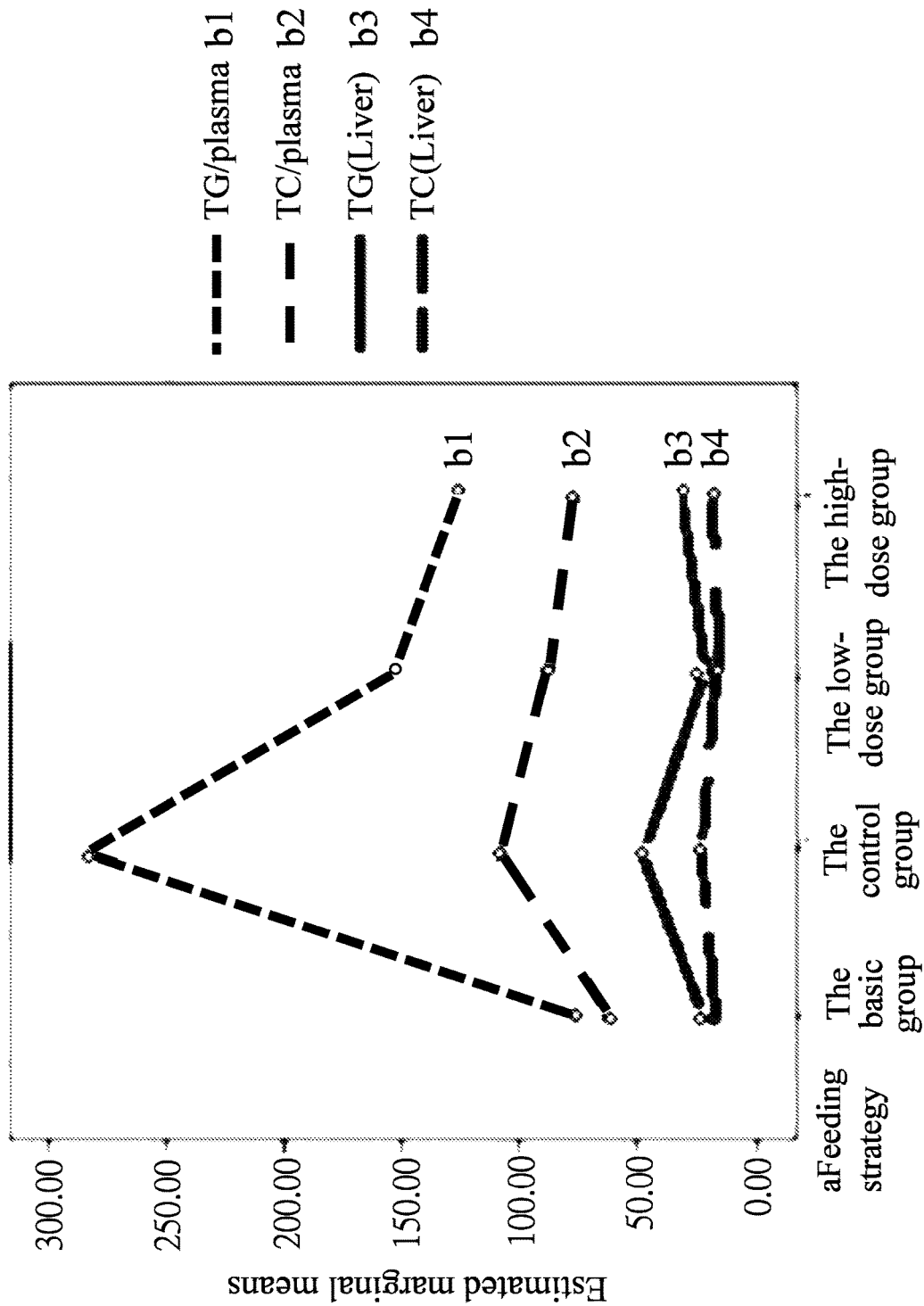
FIG. 19 and FIG. 20 are comparison diagrams of post-mortem analysis of two-factor mixed-design analysis of variance for the Longan flower extract.
Figure 20:
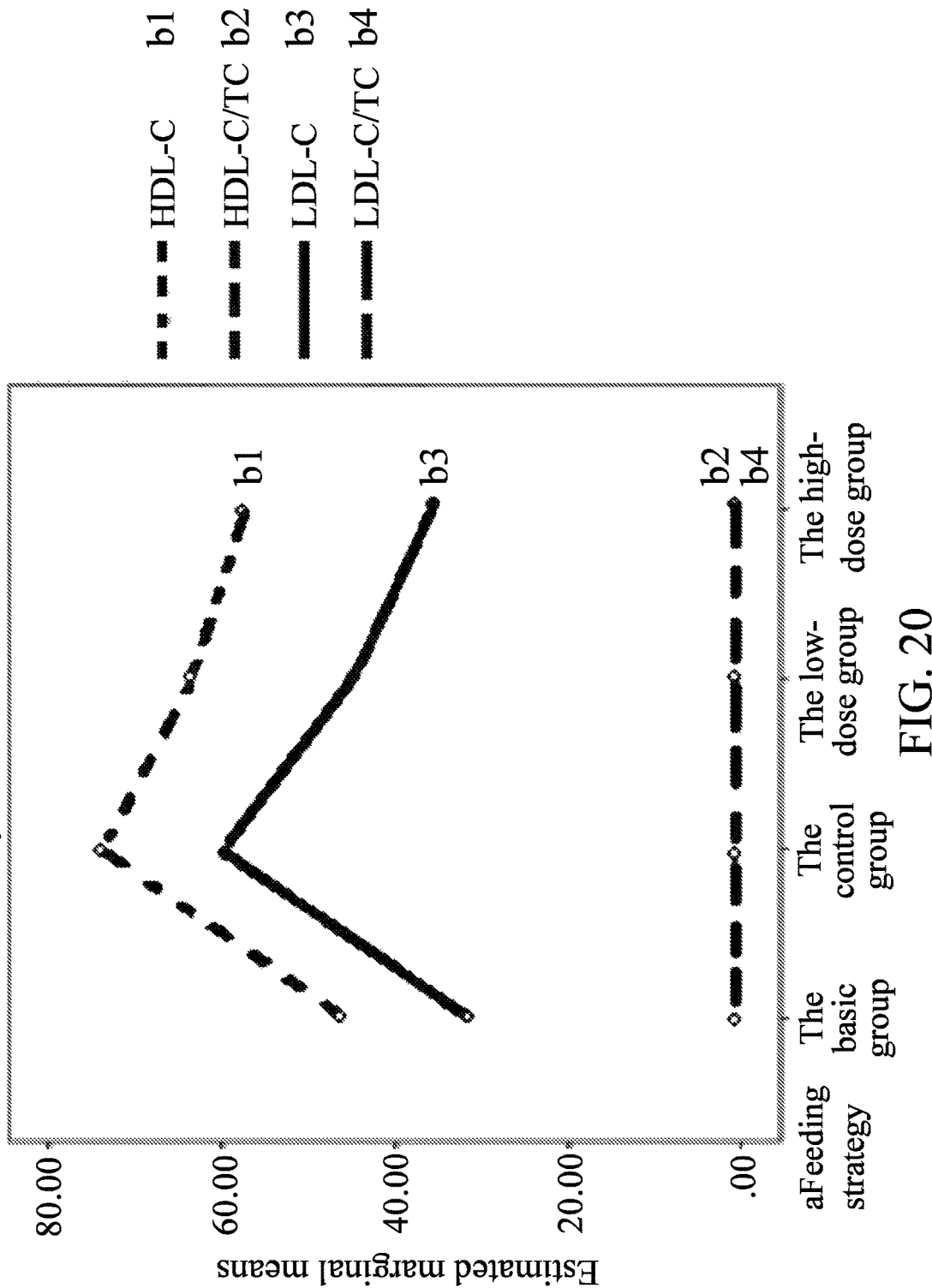

FIG. 19 and FIG. 20 are comparison diagrams of post-mortem analysis of two-factor mixed-design analysis of variance for the Longan flower extracts, which establishes lipoprotein and lipid simultaneous groups. In FIG. 19, TG/plasma and TC/plasma are significantly different, but TG(liver) and TC(liver) are not significantly different. In FIG. 20, TG/plasma and LDL-C are significantly different, but HDL-C/TC and LDL-C/TC are not significantly different.

Referring to FIG. 21 to FIG. 28, diagrams of the regression mediation of the Longan flower extracts.

Figure 21:
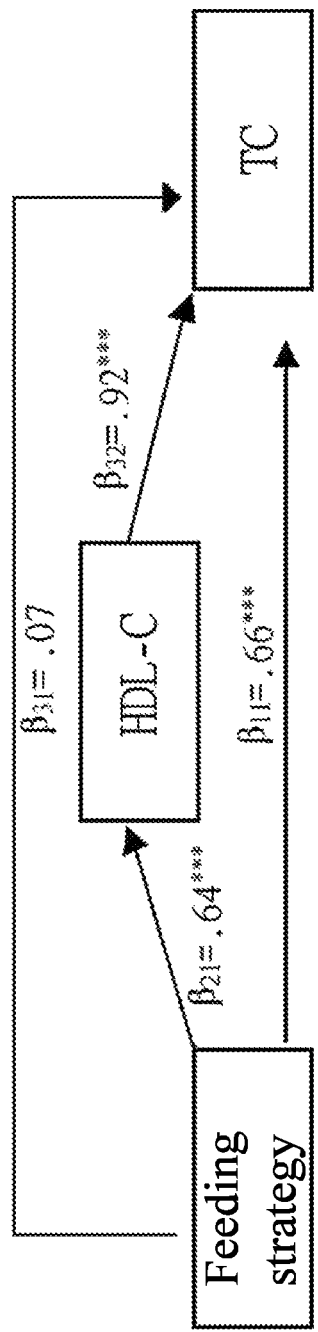
FIGS. 21 to 28 are diagrams of multiple regression mediation of the Longan flower extract.

Referring to FIG. 21, HDL has a complete mediation effect on the effect of feeding strategies on TC.

Figure 22:
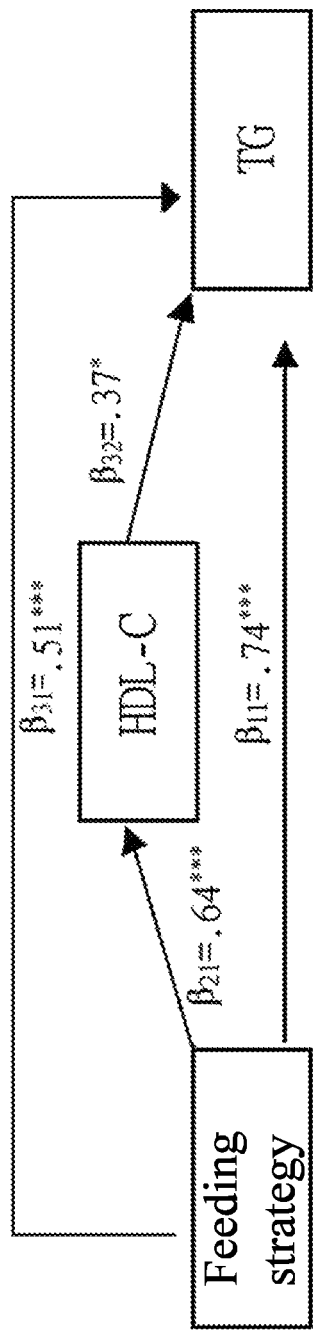

Referring to FIG. 22, HDL has a partial mediation effect on the effect of feeding strategies on TG.

Figure 23:
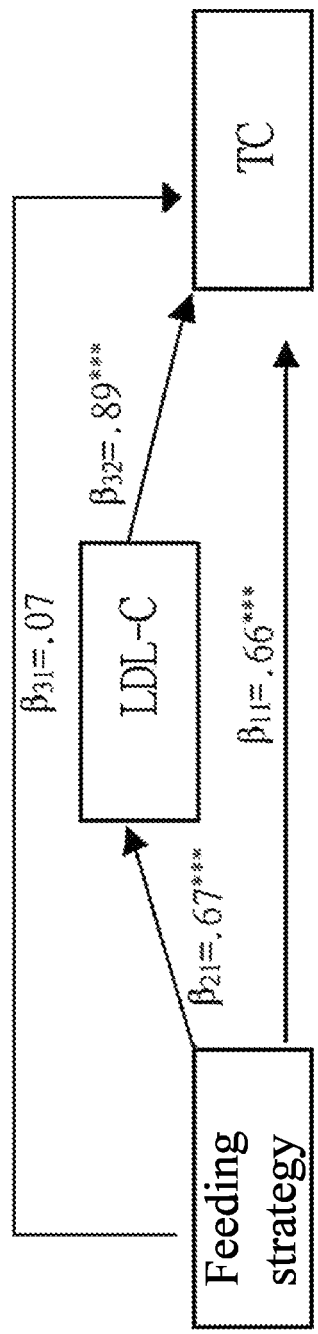

Referring to FIG. 23, LDL has a complete mediation effect on the effect of feeding strategies on TC.

Figure 24:
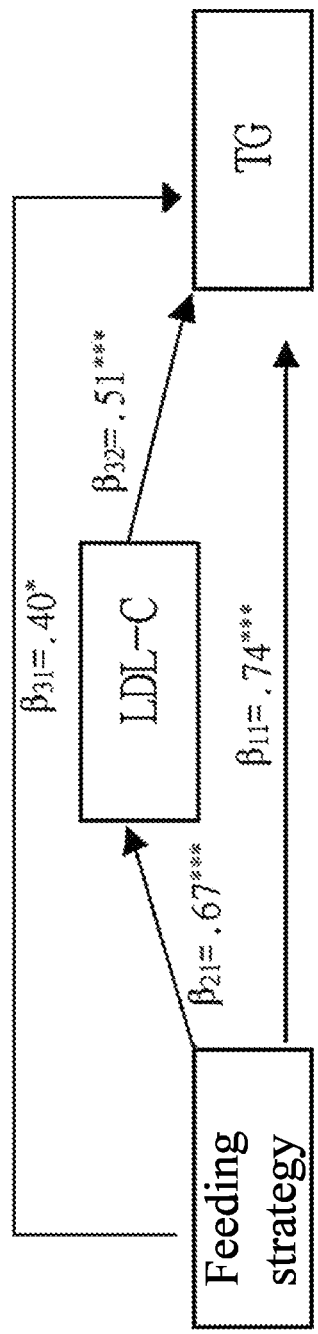

Referring to FIG. 24, LDL has a partial mediation effect on the effect of feeding strategies on TG.

Figure 25:
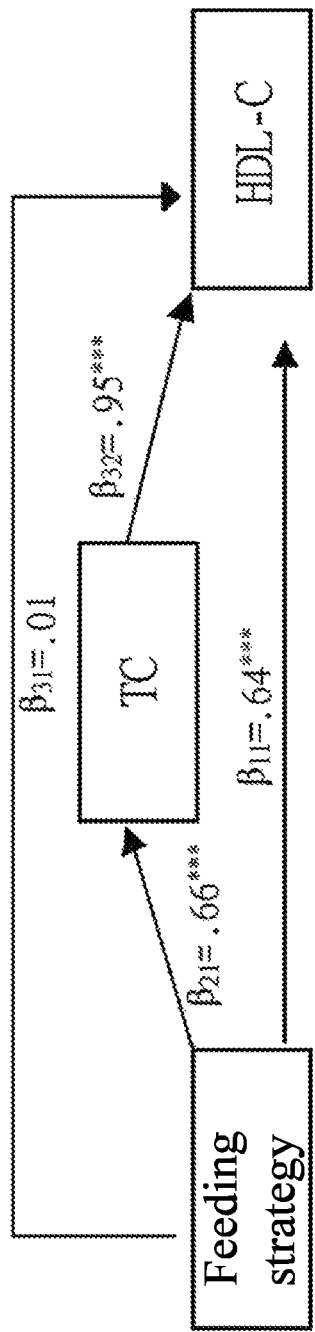

Referring to FIG. 25, TC has a complete mediation effect on the effect of feeding strategies on HDL.

Figure 26:
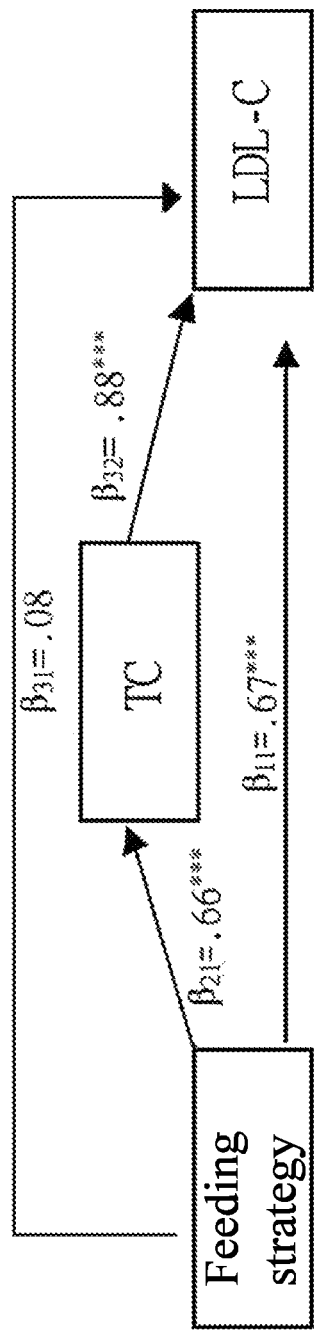

Referring to FIG. 26, TC has a complete mediation effect on the effect of feeding strategies on LDL.

Figure 27:
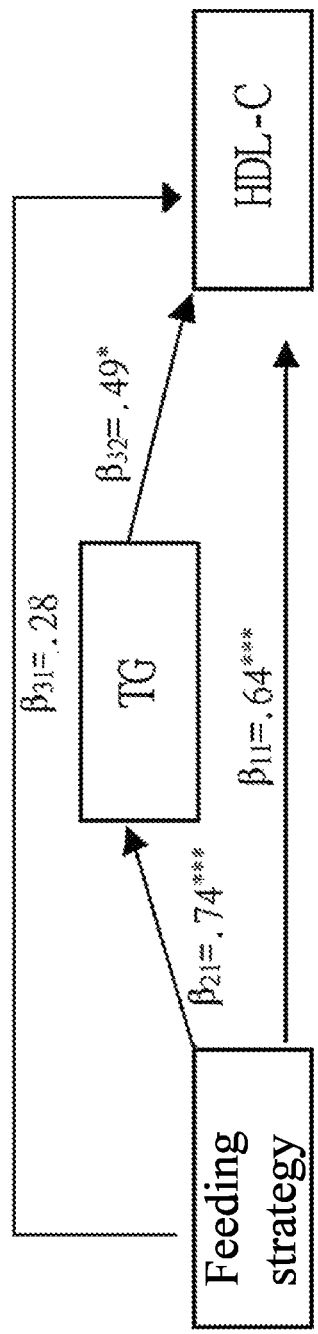

Referring to FIG. 27, TG has a complete mediation effect on the effect of feeding strategies on HDL.

Figure 28:
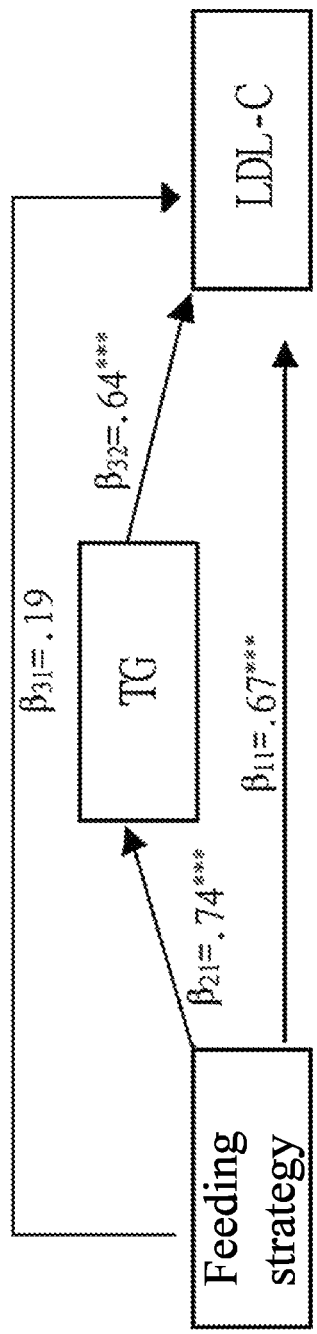

Referring to FIG. 28, TG has a complete mediation effect on the effect of feeding strategies on LDL.

FIG. 21 shows the effect of HDL-C on TC, the feeding strategy improves the effect on TC, and the direct effect is 0.06, the indirect effect is 0.60, and the total effect is 0.66.

FIG. 22 shows the effect of HDL-C on TG, the feeding strategy improves the effect on TG, and the direct effect is 0.47, the indirect effect is 0.27, and the total effect is 0.74.

FIG. 23 shows the effect of LDL-C on TC, the feeding strategy improves the effect on TC, and the direct effect is 0.08, the indirect effect is 0.58, and the total effect is 0.66.

FIG. 24 shows the effect of LDL-C on TG, the feeding strategy improves the effect on TG, and the direct effect is 0.37, the indirect effect is 0.37, and the total effect is 0.74.

FIG. 25 shows the effect of TC on HDL-C, the feeding strategy improves the effect on HDL-C, and the direct effect is 0.03, the indirect effect is 0.61, and the total effect is 0.64.

FIG. 26 shows the effect of TC on LDL-C, the feeding strategy improves the effect on LDL-C, and the direct effect is 0.08, the indirect effect is 0.59, and the total effect is 0.67.

FIG. 27 shows the effect of TG on HDL-C, the feeding strategy improves the effect on HDL-C, and the direct effect is 0.33, the indirect effect is 0.31, and the total effect is 0.64.

FIG. 28 shows the effect of TG on LDL-C, the feeding strategy improves the effect on LDL-C, and the direct effect is 0.25, the indirect effect is 0.42, and the total effect is 0.67.

Figure 29:
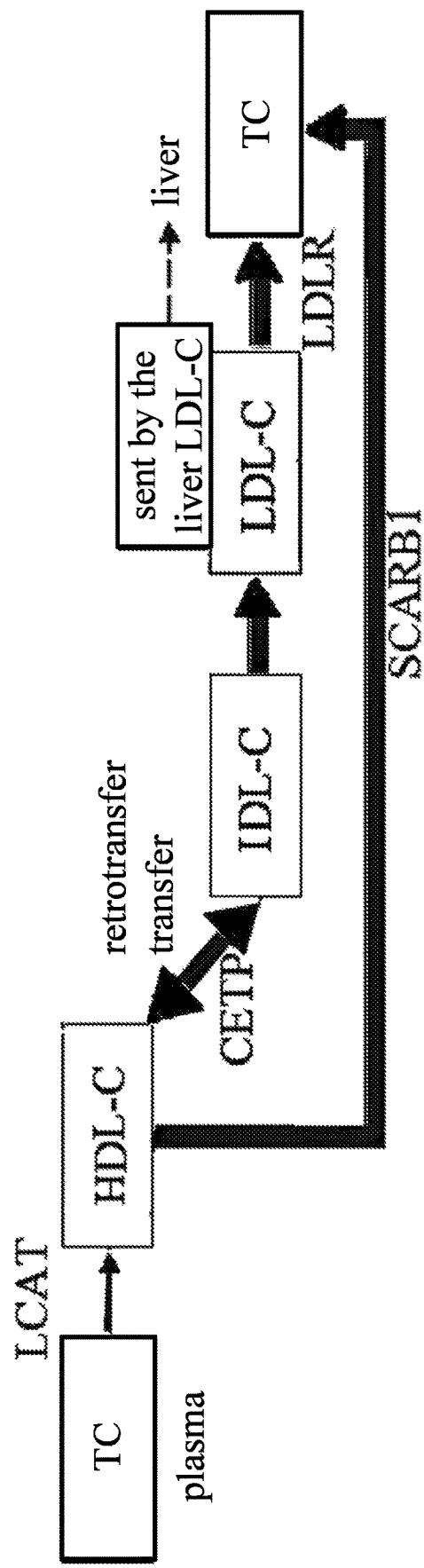
FIGS. 29 to 31 are schematic diagrams of lipoprotein and lipid metabolism relationship of the Longan flower extract.
Figure 30:
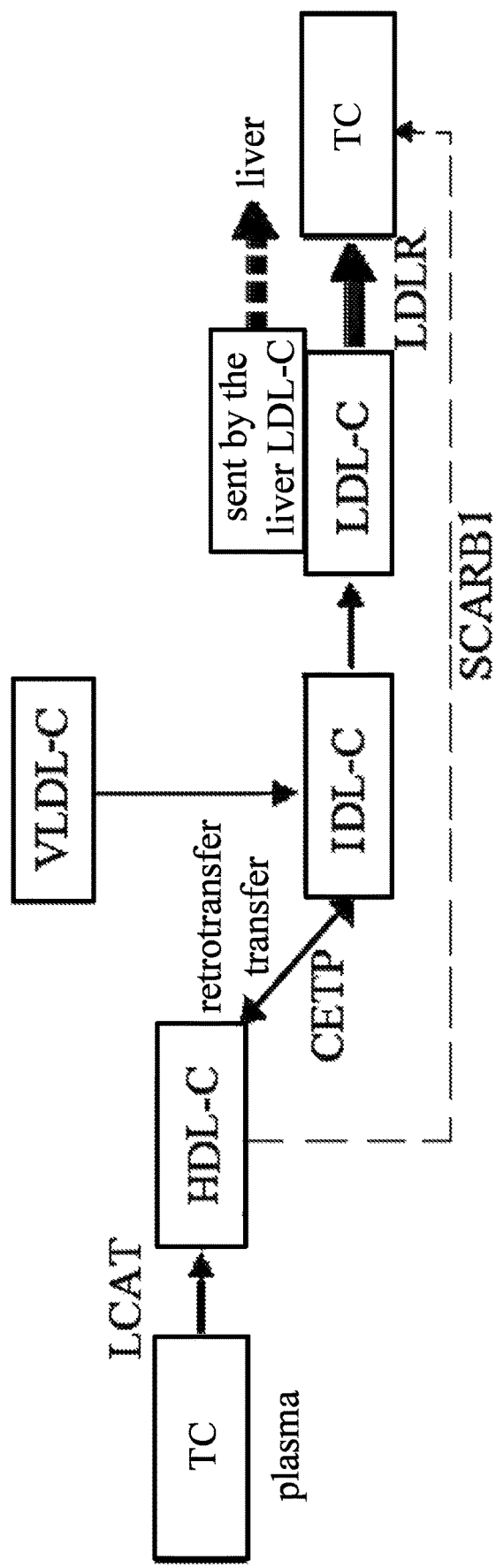
Figure 31:
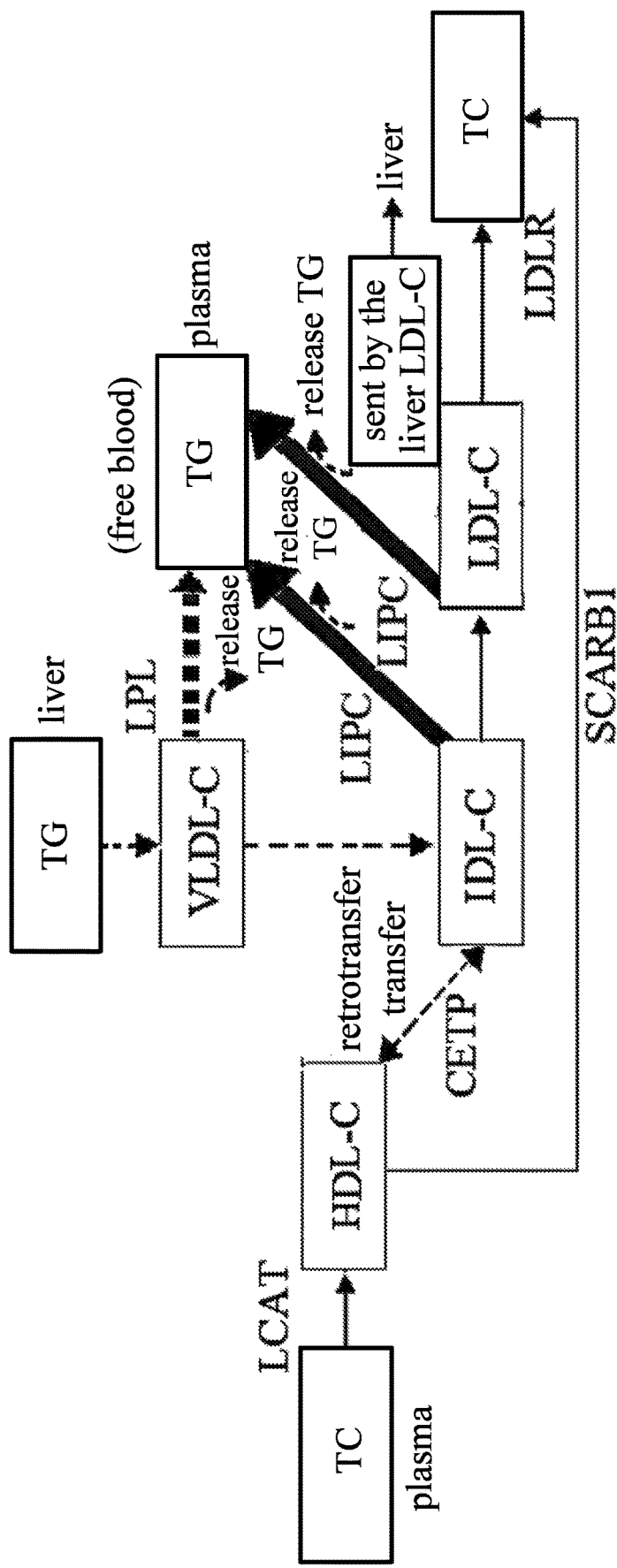

FIGS. 29 to 31 are the diagrams of lipoprotein and lipid metabolism map of Longan flower extracts.

FIG. 29 shows the effect between HDL-C and TC, FIG. 30 shows the effect between LDL-C and TC, and FIG. 31 shows the effect between HDL-C and TG and between LDL-C and TG.

Longan flower extracts can establish the relationship between LDL-C and TG metabolism, CETP inhibitor increases HDL-C/TG, so that the therapeutic effect of Longan flower extracts is inferior to the herbal formula of the present disclosure.

The therapeutic effect that Longan flower extract affects the CETP inhibitor to reduce the LDL-C concentration is inferior to the herbal formula of the present disclosure.

The therapeutic effect that Longan flower extract affects the CETP inhibitor to reduce the TC concentration is inferior to the herbal formula of the present disclosure.

Therefore, compared with the herbal formula of the present disclosure, the treatment effect of Longan flower extract is weak.

Figure 32:
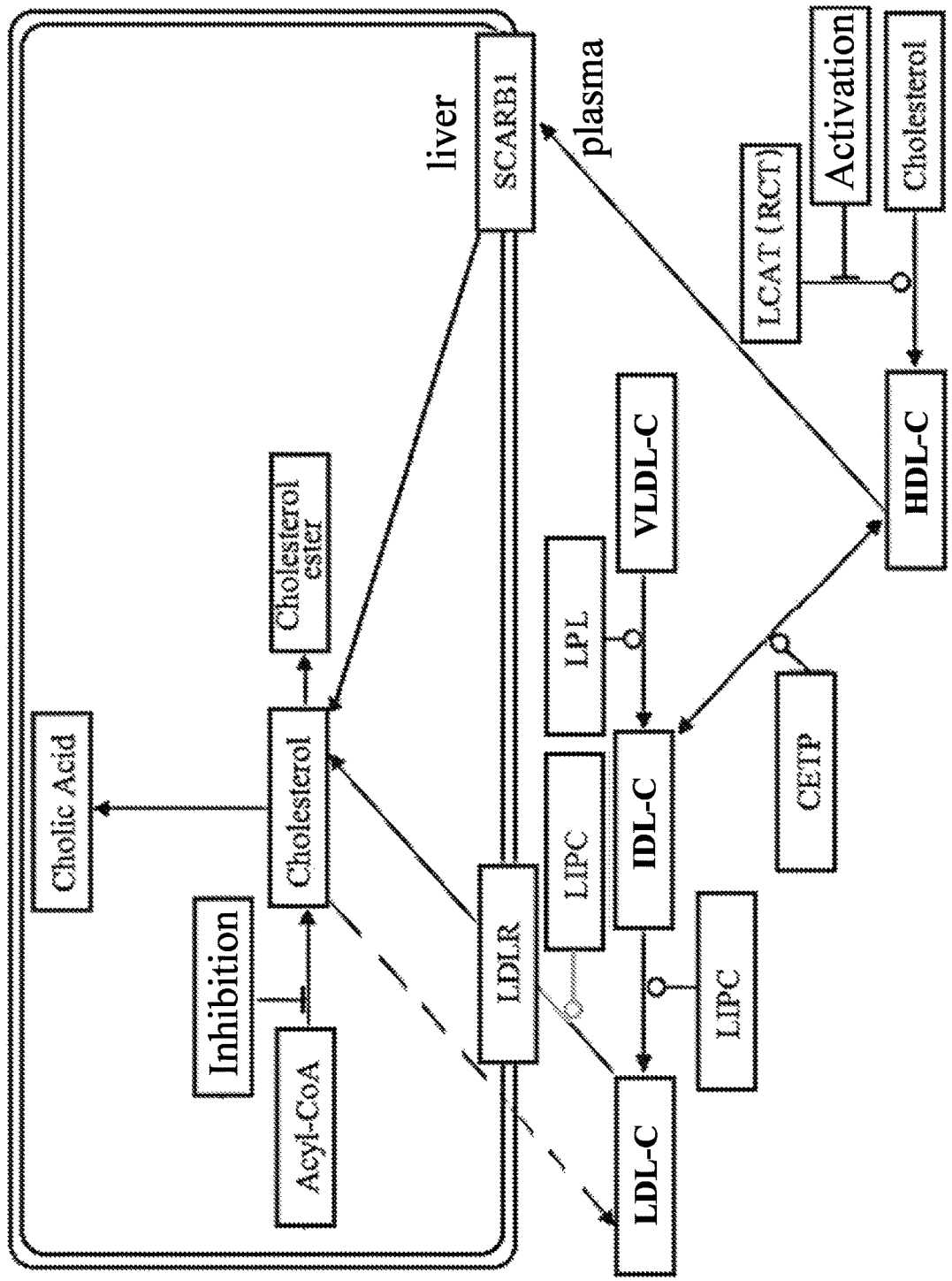
FIG. 32 and FIG. 33 are diagrams of the interaction path of blood lipid metabolism depicted by the comparison between the Longan flower extract metabolism and cholesterol drug metabolism.
Figure 33:
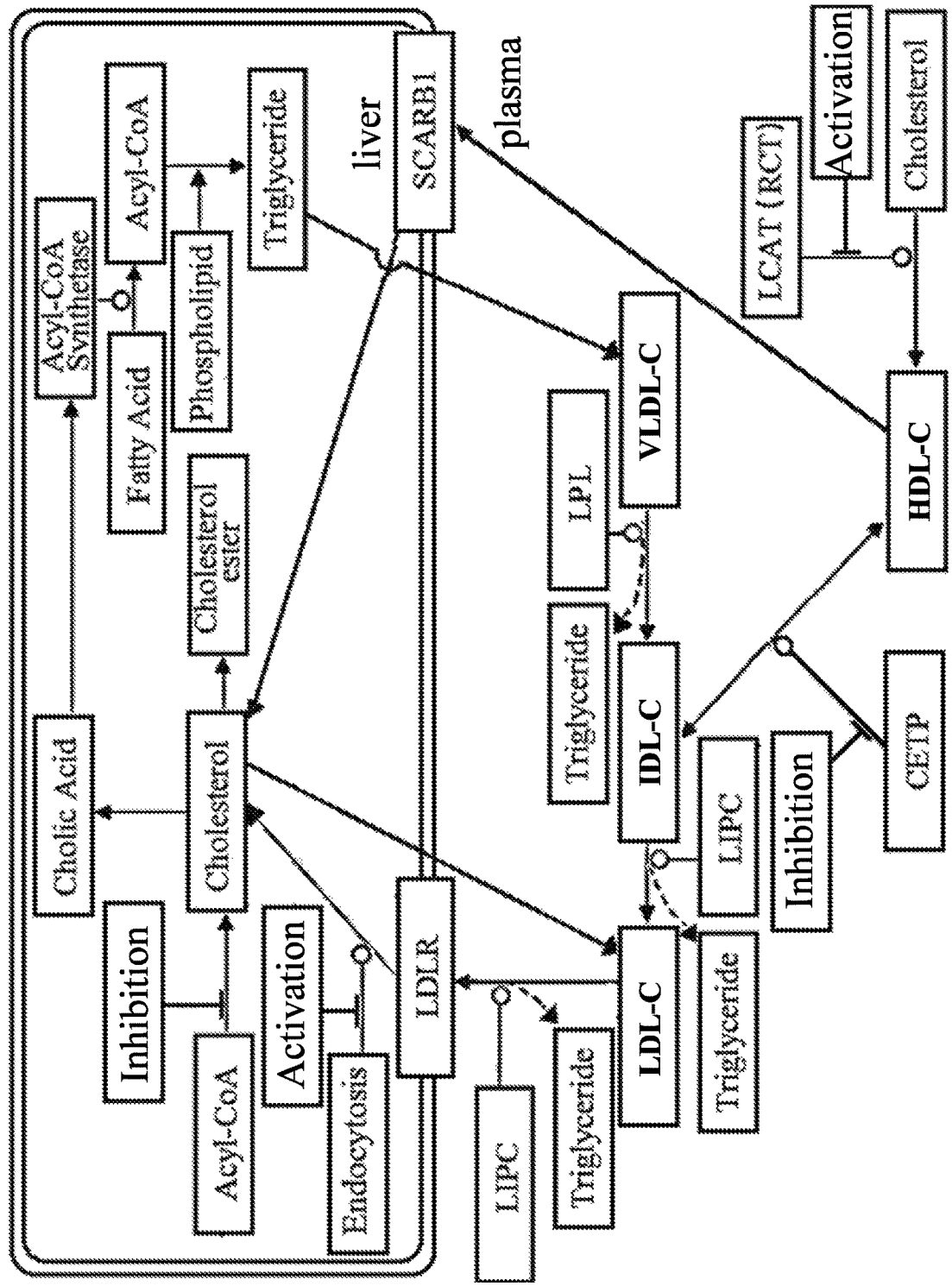

FIGS. 32 to 33 are diagrams of the interaction path of blood lipid metabolism depicted by the comparison between the Longan flower extract metabolism and cholesterol drug metabolism. HMG-CoA reductase inhibitor mainly reduces the concentration of cholesterol and even reduces the concentration of LDL-C (by inhibiting liver cholesterol synthesis and increasing the number of LDL-receptors in liver cells). CETP inhibitor is a molecule that transfers cholesterol between HDL-C and LDL-C, CETP transfers cholesterol between HDL-C and LDL-C.

Longan flower extracts can establish the relationship between LDL-C and TG metabolism, CETP inhibitor increases HDL-C/TG, so that the therapeutic effect of Longan flower extracts is inferior to the herbal formula of the present disclosure.

The therapeutic effect that Longan flower extract affects the CETP inhibitor to reduce the LDL-C concentration is inferior to the herbal formula of the present disclosure.

The therapeutic effect that Longan flower extract affects the CETP inhibitor to reduce the TC concentration is inferior to the herbal formula of the present disclosure.

Therefore, compared with the herbal formula of the present disclosure, the treatment effect of Longan flower extract is weak.

Compared with cholesterol drug metabolism, the amount of LDL-C reductions in the upper and lower pathway of the high-dose group of the Longan flower extract in the chart cannot be greater than the expected index content group reduction ratio and LDL-C cannot send away more TC in blood flowing through liver by endocytosis into liver cells.

The feeding strategy has a great ability to explain TC, the coefficient of determination is enormously powerful, has only slightly better than the expected therapeutic effect, and the ability to explain LDL-C indirectly through TC is great, and the indirect effect is great, being only slightly better than the expected indirect therapeutic effect. However, it cannot lower the TC concentration and lower the LDL-C concentration.

Describe the pathway of blood fat metabolism interaction according to the Longan flower extract, the basic group, the low-dose group and the high-dose group have higher HDL-C/TG ratios than the control group. The low-dose group and the high-dose group are lower than (cannot be equal to) the basic group. Compared with the basic group, the low-dose group and the high-dose group increased the HDL-C concentration, and compared with the control group, the HDL-C/TG ratio is increased.

By depicting the path of blood fat metabolism interaction, the high-dose group and the low-dose group can effectively improve cholesterol and triglyceride metabolism. The herbal formula of the present disclosure is superior to Longan flower extract that inhibits CETP. During the process of improvement, the exchange of HDL-C is reduced, the release of TG in the blood is reduced, and the production of HDL-C is also reduced. HDL-C increases and decreases LDL-C concentration. HDL-C increases and sends away TC in the blood. The lower the TC concentration is, the lower the LDL-C concentration is.

Figure 34:
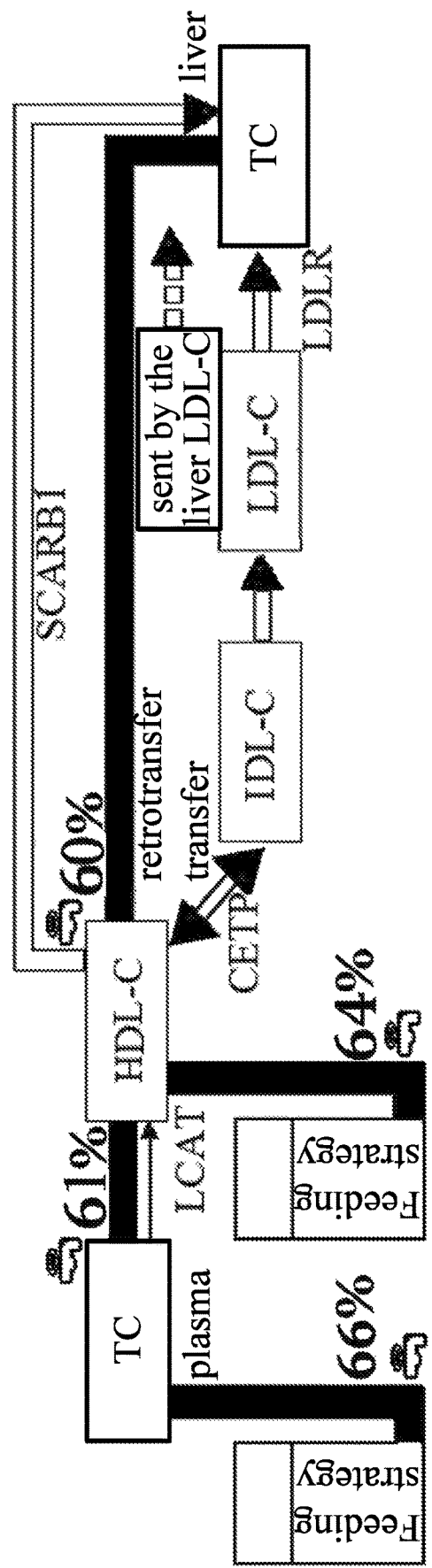
FIGS. 34 to 36 are diagrams of system dynamics established by lipoprotein-lipid complex of the Longan flower extract.
Figure 35:
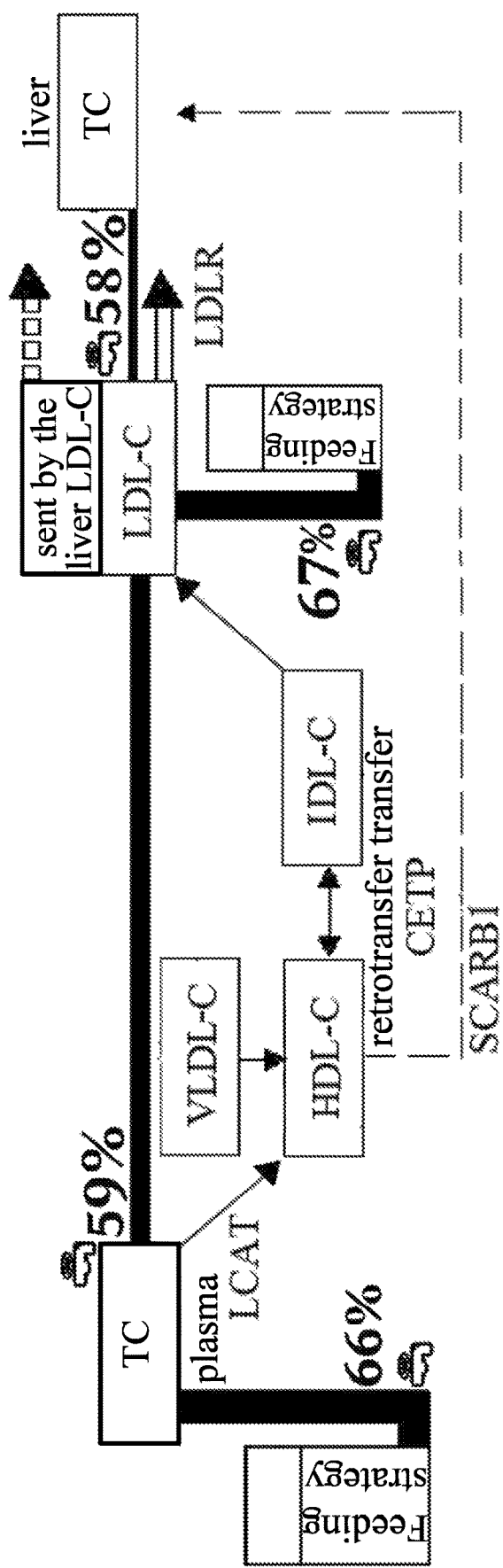
Figure 36:
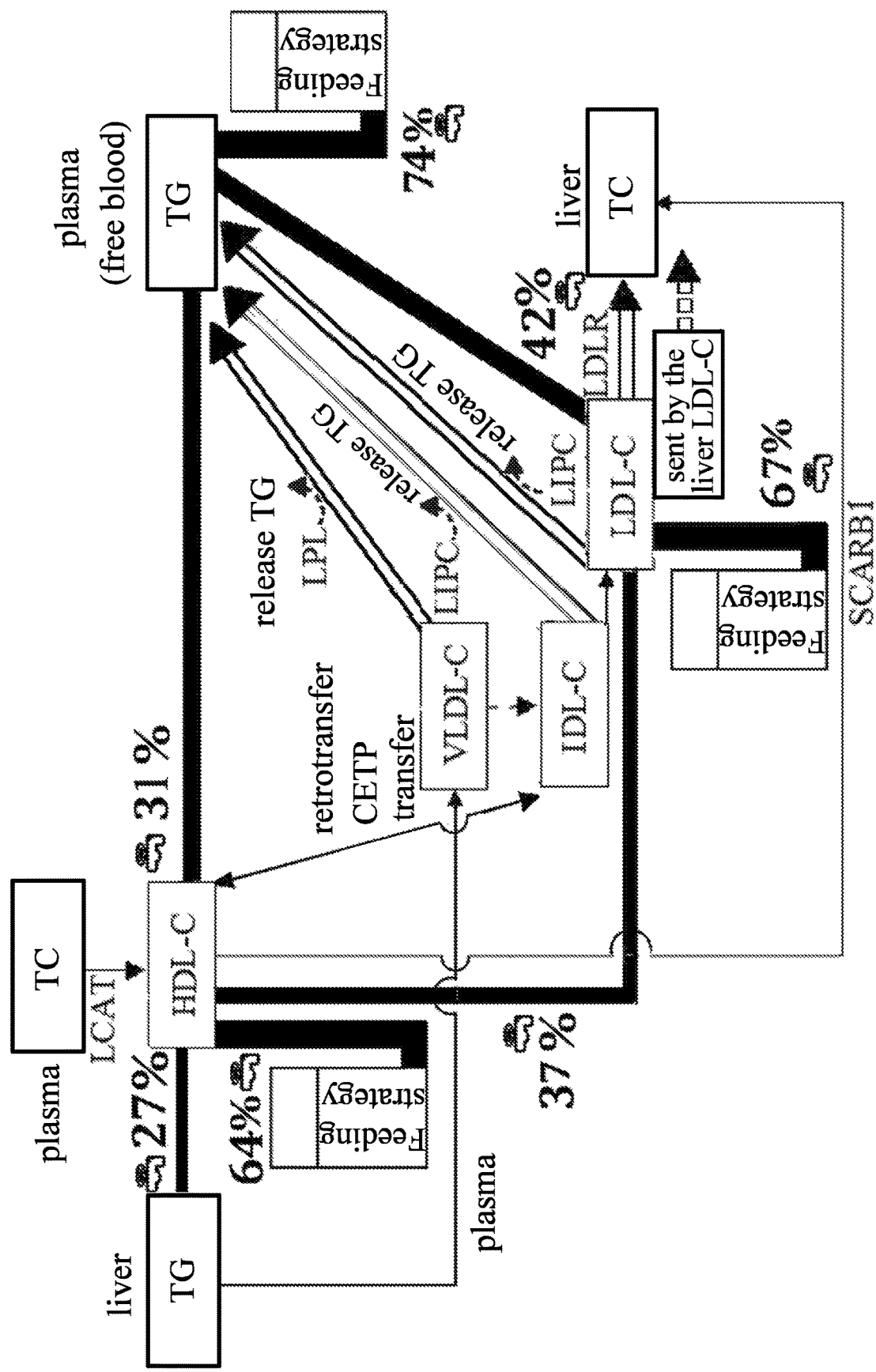

FIGS. 34 to 36 are diagrams of system dynamics established by lipoprotein-lipid complex of the Longan flower extracts.

The two examination methods of HMG-CoA reductase inhibitors include the explanatory power of the statistical relationship determination coefficient statistical model and the explanatory power of the mediating effect.

The following description describes LDL-C in the feeding strategy is determined.

The explanatory power of the statistical model is shown in Table 3, TC≈1:4.0:2.7:1.8, LDL-C≈1:4.0:2.4:1.4. However, LDL-C≈1.4 in the high-dose group is not better than TC≈1.8, the explanatory power of TC and LDL-C in the feeding strategies are similar, the coefficient of determination has the same explanatory power, and the therapeutic effect cannot be better. The amount of LDL-C in the upper and lower groups of the high-dose group cannot be reduced more than the amount of the expected index content group.

Referring to FIG. 34, the following description describes the explanatory power of mediation effect. TC has an indirect effect on LDL-C in the feeding strategy, which is 59%. LDL-C has an indirect effect on TC in the feeding strategy, which is 58%. Feeding strategies have the same ability to indirectly explain TC through LDL-C, and the indirect effects are similar. LDL-C cannot send away more TC in blood flowing through liver by endocytosis into liver cells.

Therefore, the therapeutic effect that Longan flower extract affects the HMG-CoA reductase inhibitor to reduce the LDL-C concentration is inferior to the herbal formula of the present disclosure.

The following description describes TC in the feeding strategy is determined.

Referring to Table. 3, the following description describes the explanatory power of mediation effect. The feeding strategy has an explanatory power of 0.66* on TC (as marked 66% in FIG. 35**). The high-dose and the low-dose groups of the cholesterol drug metabolism is effective for TC, but only the high dose is significantly different from the control group, and LDL-C and TC have the same situation. The feeding strategy has a very strong ability to explain TC, and the coefficient of determination is very strong, being only slightly better than expected therapeutic effects.

Referring to FIG. 35, the following description describes the explanatory power of mediation effect. LDL-C has an indirect effect on TC in the feeding strategy, which is 58%. The feeding strategy has a great ability to indirectly explain LDL-C through TC, and the indirect effect is great, being only slightly better than the expected indirect treatment effect. However, it cannot lower the TC concentration and lower the LDL-C concentration, and TC indirect interpretation of LDL-C and LDL-C indirect interpretation of TC have exactly the same situation.

Therefore, the therapeutic effect of HMG-CoA reductase inhibitor mainly reduces cholesterol concentration is equal to the herbal formula of the present disclosure. The therapeutic effect that Longan flower extract affects the HMG-CoA reductase inhibitor to reduce the LDL-C concentration is inferior to the herbal formula of the present disclosure.

The two determinations of CETP inhibitors mainly include coupling relationship and decoupling relationship Referring to FIGS. 34 to 36, the coupling relationship of TC is determined according to the system dynamics established by lipoprotein-lipid complex of the Longan flower extract.

In FIG. 34, the directionality of TC cargo and HDL-C carrier includes TC being completely mediated into HDL-C through LCAT according to the expected index content group ratio, and HDL-C being completely mediated into TC in the blood according to the expected index content group ratio.

In FIG. 35, the directionality of TC cargo and LDL-C carrier includes TC being completely mediated into LDL-C according to expected index content group ratio, and LDL-C being completely mediated into TC in the blood through the liver according to expected index content group ratio. FIG. 34 and FIG. 35 have the relationship of carrier polymer to determine the explanatory power of the direction of the regression path.

Therefore, the therapeutic effect of Longan flower extracts increasing the concentration of HDL-C is equal to the herbal formula of the present disclosure (the therapeutic effect of the high-dose group of Longan flower extracts is inferior to the herbal formula of the present disclosure). The therapeutic effect of Longan flower extracts reducing the TC concentration is equal to the herbal formula of the present disclosure, and the therapeutic effect of Longan flower extracts reducing LDL-C concentration is inferior to the herbal formula of the present disclosure.

The descriptive statistics are as follows: compared with the basic group, the high-dose group and the low-dose group of Longan flower extracts had a significant difference in increasing HDL-C. The basic group, low-dose group and high-dose group of Longan flower extracts have higher HDL-C/TG ratios than the control group. The high-dose group and the low-dose group of Longan flower extracts increased HDL-C concentration compared with the basic group and increased HDL-C/TG ratio compared with the control group. The directional influence of the regression path can prove that the high-dose group and the low-dose group of Longan flower extracts meet the characteristics of CETP inhibitors. However, the therapeutic effects of the low-dose and high-dose of Longan flower extracts are not as good as the herbal formula of the present disclosure to increase HDL-C/TG ratio.

Therefore, the therapeutic effect of Longan flower extracts increasing HDL-C/TG ratio is inferior to the herbal formula of the present disclosure.

Referring to FIGS. 34 to 36, the uncoupling relationship is determined according to the system dynamics established by lipoprotein-lipid complex of the Longan flower extract.

In FIG. 36, the directionality of TG cargo and HDL-C carrier includes that TG released in the blood is partially mediated by HDL-C from the blood according to the expected index content group ratio and HDL-C in the blood completely mediates TG released in the blood according to the expected index content.

In the effect of HDL-C, the TG of Longan flower extracts has a completely mediated effect, and the therapeutic effect is inferior to the TG of the herbal formula of the present disclosure, which has a partial mediated effect. In the effect of TG, the HDL-C of Longan flower extracts has a partial mediated effect, and the therapeutic effect is equal to the HDL-C of the herbal formula of the present disclosure, which has a partial intermediate mediated effect.

Therefore, the therapeutic effect of CETP inhibitor of Longan flower extracts to increase the concentration of HDL-C is equal to the herbal formula of the present disclosure (the therapeutic effect of the high-dose group of Longan flower extracts is inferior to the herbal formula of the present disclosure). The therapeutic effect of CETP inhibitor of Longan flower extracts to increase HDL-C/TG ratio is inferior to the herbal formula of the present disclosure. The therapeutic effect of CETP inhibitors of Longan flower extracts mainly to reduce the concentration of TG is inferior to the herbal formula of the present disclosure.

In FIG. 36, the directionality of TG cargo and LDL-C carrier includes that TG released in the blood is partially mediated by LDL-C from the blood according to the expected index content group ratio and LDL-C in the blood completely mediates TG released in the blood according to the expected index content.

The therapeutic effect of CETP inhibitor of Longan flower extracts to reduce LDL-C concentration is inferior to the herbal formula of the present disclosure. The therapeutic effect of CETP inhibitor of Longan flower extracts to reduce TG concentration is inferior to the herbal formula of the present disclosure.

According to the analysis of Longan flower extract, Longan flower extract can still establish LDL-C and TG metabolism, resulting in the therapeutic effect of CETP inhibitors to increase the HDL-C/TG ratio is inferior to the herbal formula of the present disclosure. The therapeutic effect of CETP inhibitor of Longan flower extracts to increase the concentration of HDL-C is equal to the herbal formula of the present disclosure (the therapeutic effect of the high-dose group of Longan flower extracts is inferior to the herbal formula of the present disclosure). The therapeutic effect of CETP inhibitor of Longan flower extracts to reduce LDL-C concentration is inferior to the herbal formula of the present disclosure. The therapeutic effect of CETP inhibitor of Longan flower extracts to reduce TG concentration is inferior to the herbal formula of the present disclosure.

The descriptive statistics are as follows: compared with the basic group, the high-dose group and the low-dose group of Longan flower extracts had a significant difference in increasing HDL-C. The basic group, low-dose group and high-dose group of Longan flower extracts have higher HDL-C/TG ratio than the control group. The high-dose group and the low-dose group of Longan flower extracts increased HDL-C concentration compared with the basic group and increased HDL-C/TG ratio compared with the control group. The directional influence of the regression path can prove that the high-dose group and the low-dose group of Longan flower extracts meet the characteristics of CETP inhibitors. However, the therapeutic effects of the low-dose and high-dose of Longan flower extracts are not as good as the herbal formula of the present disclosure to increase HDL-C/TG ratio.

Partially mediated effect results from the HDL-C and TG concentrations are highest in the control group and lowest in the basic group, causing TG to affect HDL-C more than HDL-C affects TG. TG has complete mediating effect on HDL-C. HDL-C has partial mediating effect on TG.

While the high-dose group of Longan flower extracts meets the characteristics of CETP inhibitor, TG has a complete mediating effect on HDL-C. Therefore, the therapeutic effect of CETP inhibitor of Longan flower extracts increasing the concentration of HDL-C is equal to the herbal formula of the present disclosure (the therapeutic effect of the high-dose group of Longan flower extracts is inferior to the herbal formula of the present disclosure). The therapeutic effect of CETP inhibitor of Longan flower extracts to increase HDL-C/TG ratio is inferior to the herbal formula of the present disclosure. The therapeutic effect of CETP inhibitors of Longan flower extracts mainly to reduce the concentration of TG is inferior to the herbal formula of the present disclosure.

The descriptive statistics are as follows: partially mediated effect results from the LDL-C and TG concentrations are highest in the control group and lowest in the basic group that causes TG to affect LDL-C more than LDL-C affects TG. TG has complete mediating effect on LDL-C. LDL-C has partial mediating effect on TG Therefore, the therapeutic effect of CETP inhibitor of Longan flower extracts to increase the concentration of HDL-C is equal to the herbal formula of the present disclosure (the therapeutic effect of the high-dose group of Longan flower extracts is inferior to the herbal formula of the present disclosure). The therapeutic effect of CETP inhibitors of Longan flower extracts mainly to reduce the concentration of TG is inferior to the herbal formula of the present disclosure.

In summary, according to the analysis of Longan flower extract, the therapeutic effect produced by using Longan flower extract to inhibit the HMG-CoA reductase so as to reduce the TC concentration is equal to the herbal formula of the present disclosure. The therapeutic effect produced by using Longan flower extract to inhibit the HMG-CoA reductase so as to reduce the LDL-C concentration is inferior to the herbal formula of the present disclosure. The therapeutic effect of Longan flower extracts increasing the concentration of HDL-C is equal to the herbal formula of the present disclosure (the therapeutic effect of the high-dose group of Longan flower extracts is inferior to the herbal formula of the present disclosure). The therapeutic effect of Longan flower extracts increasing HDL-C/TG ratio is inferior to the herbal formula of the present disclosure. The therapeutic effect of CETP inhibitors of TG of Longan flower extracts mainly to reduce the concentration is inferior to the herbal formula of the present disclosure.

Therefore, the herbal formula of the present disclosure can reduce cholesterol and triglyceride, and can be used to prepare a pharmaceutical composition as an HMG-CoA reductase inhibitor and a CETP inhibitor for preventing and treating metabolic syndrome.

Advantageous Effects of the Embodiment

One of the advantages of the present disclosure is that, the herbal formula used for preparing a pharmaceutical composition for preventing and treating metabolic syndrome of the present disclosure can improve conditions of overweight, hyperglycemia, fatty liver, dyslipidemia, hypercholesterolemia, or hypertriglyceridemia through the technical solution of "the herbal formula comprises *Rehmanniae radix preparata, Cornus officinalis, Dioscorea polystachya, Alisma plantago-aquatica, Paeonia suffruticosa, Poria cocos, Aconitum carmichaeli*, and *Cinnamomum cassia*".

Furthermore, the pharmaceutical composition prepared by the herbal formula of the present disclosure can be used alone, and the effect of preventing and treating metabolic syndrome can be achieved without adding other effective active ingredients. It is worth noting that general medicines can usually only reduce the triglyceride or cholesterol of the acceptor, while the herbal formula of the present disclosure can reduce both of triglyceride and cholesterol of the acceptor at the same time (belonging to a synergistic effect), so as to achieve the effect of effectively improving the metabolic syndrome.

Moreover, the herbal formula of the present disclosure can reduce cholesterol and triglyceride, and can be used to prepare a pharmaceutical composition as an HMG-CoA reductase inhibitor and a CETP inhibitor for preventing and treating metabolic syndrome.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. An herbal formula used for preparing a pharmaceutical composition for preventing and treating metabolic syndrome, wherein the herbal formula comprises therapeutically effective amounts of *Rehmanniae radix preparata, Cornus officinalis, Dioscorea polystachya, Alisma plantago-aquatica, Paeonia suffruticosa, Poria cocos, Aconitum carmichaeli*, and *Cinnamomum cassia*.

2. The herbal formula used for preparing the pharmaceutical composition for preventing and treating metabolic syndrome according to claim 1, wherein the herbal formula is composed of the following components: 25-35 wt % of *Rehmanniae radix preparata*, 12-18 wt % of *Cornus officinalis*, 12-18 wt % of *Dioscorea polystachya*, 7-13 wt % of *Alisma plantago-aquatica*, 7-13 wt % of *Paeonia suffruticosa*, 7-13 wt % of *Poria cocos*, 2-6 wt % of *Aconitum carmichaeli*, and 2-6 wt % of *Cinnamomum cassia*.

3. The herbal formula used for preparing the pharmaceutical composition for preventing and treating metabolic syndrome according to claim 2, wherein the herbal formula is composed of the following components: 29.6 wt % of *Rehmanniae radix preparata*, 14.8 wt % of *Cornus officinalis*, 14.8 wt % of *Dioscorea polystachya*, 11.1 wt % of *Alisma plantago-aquatica*, 11.1 wt % of *Paeonia suffruticosa*, 11.1 wt % of *Poria cocos*, 3.7 wt % of *Aconitum carmichaeli*, and 3.7 wt % of *Cinnamomum cassia*.

4. The herbal formula used for preparing the pharmaceutical composition for preventing and treating metabolic syndrome according to claim 1, wherein the prevention and treatment of metabolic syndrome refers to therapeutic effects that are capable of improving conditions of overweight, hyperglycemia, fatty liver, dyslipidemia, hypercholesterolemia, or hypertriglyceridemia.

5. The herbal formula used for preparing the pharmaceutical composition for preventing and treating metabolic syndrome according to claim 4, wherein the prevention and treatment of metabolic syndrome is achieved by the simultaneous inhibition of 3-hydroxy-3-methylglutaryl coenzyme A reductase and cholesteryl ester transfer protein by the herbal formula.

6. The herbal formula used for preparing the pharmaceutical composition for preventing and treating metabolic syndrome according to claim 1, wherein the pharmaceutical composition is administered orally to a recipient at 10-40 g per day.

7. The herbal formula used for preparing the pharmaceutical composition for preventing and treating metabolic syndrome according to claim 1, wherein a dosage form of the pharmaceutical composition is powder, water extract solution, suspension, emulsion, syrup, pill, tablet, hydrogel, or capsule.

8. The herbal formula used for preparing the pharmaceutical composition for preventing and treating metabolic syndrome according to claim 1, wherein the pharmaceutical composition further includes a pharmaceutically acceptable adjuvant.

* * * * *